US006601010B1

United States Patent
Fowler et al.

(10) Patent No.: US 6,601,010 B1
(45) Date of Patent: Jul. 29, 2003

(54) FORCE PLATE ACTOMETER

(75) Inventors: Stephen C. Fowler, Lawrence, KS (US); Troy Zarcone, Prairie Village, KS (US)

(73) Assignee: The University of Kansas, Lawrence, KS (US)

( * ) Notice: Subject to any disclaimer, the term of this patent is extended or adjusted under 35 U.S.C. 154(b) by 171 days.

(21) Appl. No.: 09/586,899

(22) Filed: Jun. 5, 2000

(51) Int. Cl.$^7$ .............................................. B63C 11/02
(52) U.S. Cl. ......................... 702/139; 702/131; 702/79
(58) Field of Search .................. 702/139, 131, 702/79; 600/544; 119/103; 128/779; 422/58

(56) References Cited

U.S. PATENT DOCUMENTS 5,388,591 A * 2/1995 De Luca et al. ............ 128/779

OTHER PUBLICATIONS

Stazione zoologica anton dohrn–activity report 1991, Behavioural aspects in marine invertebrates, Dr. G. Fiorito, Prof. P Scotto, http://www.szn.it/actrep91/contents.htm.*
Web page Laboras Product Information dated Aug. 24, 2000.
Modular Research Systems Catalog, pp. 30–34 "Open Field Activity" and "RotoRat™ Rotational Activity" by Med Associates, Inc.
Lafayette Instrument Catalog, 25$^{th}$ Ed., Animal Sciences, pp. 13 and 14 "Activity Monitoring".
Stoelting Catalog, Items #9 and 10 re Hole Board 56650 and Activity Cage 57400.
Noldus Product Brochure re EthoVision® for Windows.
Coulbourn Instruments "Response" Jun. 1999 Newsletter.
Web page re RotoScan Rotometer dated May 3, 2000.
Web page re The Digiscan Line of Animal Activity Monitors dated May 14, 2000.

Young et al.; A New Utltrasonic Method for Measuring Minute Motion Activities on Rats, *J. Neuroscience Methods*, 70:45–49 (1996).

Canales et al.; A Measure of Striatal Function Predicts Motor Stereotypy; *Nature Neuroscience*, 3(4):377–383 (Apr. 2000).

Abstract—Barwick et al.; Subthalamic nucleus microinjections of 5–HT2 receptor antagonists suppress stereotypy in rats; *Neuroreport*, Feb. 7, 2000; 11(2):267–70.

Abstract—Rigdon et al.; 1192U90 in animal tests that predict antipsychotic efficacy, anxiolysis and extrapyramidal side effects; *Neuropsychopharmacology* Sep. 1996; 15(3):231–42.

(List continued on next page.)

*Primary Examiner*—John S. Hilten
*Assistant Examiner*—Tung S Lau
(74) *Attorney, Agent, or Firm*—Hovey Williams LLP

(57) ABSTRACT

A force plate actometer apparatus (30) is provided which is designed for the efficient and accurate testing of in vivo subjects (e.g., rats and mice) under the influence of drugs or other stimuli, and permits simultaneous determination of a number of attributes of movement of the subjects. The apparatus (30) includes a force plate (32), a plurality of transducers (46) supporting the plate (32), and a computer (40) coupled to the outputs of the transducers (46); an enclosure (38) is positioned above the plate (32) so as to confine the test subjects to a predetermined test area. Preferred software programs (4PLATES.PAS and OFFLINP.PAS) permit calculation and recording of test subject movement attributes derived from the variation over time of the location and/or magnitude of force exerted by the test subject on the plate (32). Such attributes may include the position of the subject on the plate, distance traveled over a defined period, the angle and direction of rotation of movement, spatial statistic, stereotypy score, tremor, wall rearing and rhythmic behaviors.

25 Claims, 21 Drawing Sheets

OTHER PUBLICATIONS

Abstract—Szewczak et al.; The pharmacological profile of iloperidone, a novel atypical antipsychotic agent; *J. Pharmacol Exp. Ther*, Sep. 1995; 274(3):1404–13.

Abstract—Gattaz et al.; Effects of zotepine, haloperidol and clozapine on MK–801–induced stereotypy and locomotion in rats; *J. Neural Transm Gen Sect* 1994; 96(3):227–32.

Abstract—Mueller; Locomotor stereotypy is produced by methylphenidate and amfonelic acid and reduced by haloperidol but not clozapine or thioridzaine; *Pharmacol Biochem Behav* May 1993; 45 (1):71–6.

Abstract; Hoffman; Typical and atypical neuroleptics antagonize MK–801–induced locomotion and stereotypy in rats; *J. Neural Transm Gen Sect*; 1992; 89(1–2):1–10.

Abstract; Schultz et al.; Prenatal protein restriction increases sensitization to cocaine–induced stereotypy; *Behav. Pharmacol Jul.* 1999: 10(4):379–87.

Abstract: Byrnes et al.; Inhibition of nitric oxide synthase in the ventral tegmental area attenuates cocaine sensitization in rats; *Prog. Neuropsychopharmacol biol Psychiatry*; Feb. 2000; 24(2):261–73.

Gothoni et al.; Quantification of Tremor in Rats Induced by Physostighmine; *Psychopharmacology* (1981) 74:275–279.

Gothoni et al.; Drugs for Parkinson's Disease Reduce Tremor Induced by Physotigmine; *Naunyn–Schmiedeberg's Arch Pharmacol.* (1981) 323:205–210.

Young et al.; A combined system for measuring animal motion activities; *J. Neuroscience Methods* 95 (2000) 55–63.

Ponas et al.; A new precise microcomputer based rotometer; *J. Neuroscience Methods*, 32 (1990) 155–158.

Schmidt et al.; A computer–based rotation and activity monitor for non–human primates and other animals; *J. Neuroscience Methods*, 24 (1988) 243–251.

Pan et al.; A new video path analyzer to monitor travel distance, rearing, and stereotypic movement of rats; *J. Neuroscience Methods, 70 (1996) 39–43*.

Martin et al.; A combined electrophysiological and video data acquisition system using a single computer; *J. Neuroscience Methods*, 92 (1999) 169–171.

Kao et al.; A new automated method for detection and recording of animal moving path; *J. Neuroscience Methods*, 63 (1995) 205–209.

Brodkin et al.; A novel apparatus for measuring rat locomotor behavior; *J. Neuroscience Methods*; 57 (1995) 171–176.

Schwarting et al.; A video image analyzing system for a open–field behavior in the rat focusing on behavioral asymmetries; *J. Neuroscience Methods*, 49 (1993) 199–210.

Prakriya et al.; A computerized grid walking system for evaluating the accuracy of locomotion in rats; *J. Neuroscience Methods*, 48 (1993) 15–25.

Bertelli et al.; Behavioral evaluating methods in the objective clinical assessment of motor function after experimental brachial plexus reconstruction in the rat; *J. Neuroscience Methods*, 46 (1993) 203–208.

Bonatz et al.; Video image analysis of behavior by microcomputer: categorization of turning and locomotion after 6–OHDA injection into the substantia nigra; *J. Neuroscience Methods*, 22 (1987) 13–26.

* cited by examiner

Amphetamine: Thick
Saline: Thin

FIG.5 Examples of Harmaline-induced tremor

Sham Surgery, Amphetamine 3.0 mg/kg,

6-OHDA Lesion, Amphetamine 3.0 mg/kg,

FORCE PLATE ACTOMETER

BACKGROUND OF THE INVENTION

1. Field of the Invention

The present invention is broadly concerned with a new instrument and method useful in behavioral neuroscience and psychopharmacological research typically involving in vivo test subjects such as rats or mice. More particularly, the invention pertains to a combined actometric and ergometric locomotor activity-measuring device referred to as a "force plate actometer," which can simultaneously perform functions now requiring three or more separate instruments. The force plate actometer is operable to determine on a real time basis variations in location and/or magnitude of the force exerted by a test subject on the device. With this information, it is possible to determine and quantify a number of different movements or sequences of movements of a test subject, such as tremor, rearing, velocity of locomotion, tendency to turn right or left and stereotypies.

2. Description of the Prior Art

The fields of behavioral neuroscience, psychopharmacology, toxicology and physiology often make use of in vivo test animals, most commonly rats and mice. Such animals are treated with experimental drugs or subjected to experimental procedures, whereupon one or more locomotor activities of the animals are observed and quantified. This type of research is often carried out in studies of genetics of Alzheimer's disease, behavioral genetics involving gene knockout mice bearing on a large number of central nervous system diseases, animal models of addiction, compounds to combat drug abuse, antischizophrenia drug discovery, research on the genetic determinants of ethanol sensitivity, Parkinson's disease research, animal models of mental retardation, self-injurious behavior, attention deficit disorder, learning disorders, neurotoxicology and virtually all central nervous system drug discovery research.

A number of different devices are used by researchers in these fields to measure animal locomotor activity. For example, one popular instrument is a photobeam actometer which detects animal activity via a grid of IR beams. Movement of the animal within the device causes some of these beams to be broken, thus revealing the animal's position in the X, Y plane. These devices also include an optional vertical Z axis activity sensor to monitor rearing or jumping activity. In these types of devices, the spatial resolution is fixed by the distance between photoemitter-detector pairs, typically 2.5 cm, giving a spatial resolution on the order of about 2.5 cm.

However, photobeam actometers are inherently limited in that they cannot simultaneously detect and quantify a variety of other motions of a test animal. Therefore, other types of activity-measuring devices have been developed, including single force transducer ergometric activity chambers (ergometric in this context meaning the measurement of energy expenditure), and video-based tracking systems for subjects where a video camera is mounted above the chamber and records the animal's movement. However, none of these devices is well suited for quantifying rat stereotypies, and neither can quantify drug-induced or lesion-induced tremor. Rotometers have also been developed which are designed to measure the number of rotations of an animal. These devices include a harness fitted to the animal with the harness being attached to a rotary counter. This eliminates the need for a human observer to count the number of turns. However, the presence of the harness serves as an animal constraint, making it difficult to know the effect of the harness on animal activity. Furthermore, these rotometers are incapable of simultaneously measuring other locomotor activities.

There is accordingly a real and unsatisfied need in the art for improved animal testing devices which can simultaneously and in real time detect and quantify a variety of different possible locomotor activities, thereby eliminating the need for extra testing equipment and the respective tests each individual instrument requires.

SUMMARY OF THE INVENTION

The present invention overcomes the problems outlined above, and provides an in vivo force plate actometer testing device in the form of a plate presenting an upper surface adapted to support a test subject, with at least three (and preferably four) transducers operably coupled with the plate at fixed relative locations. The transducers are each operable to sense a parameter resulting from movement of a test subject on the plate, and to generate an output correlated with the sensed parameter. A processor (typically a PC) is coupled with the transducers to receive the outputs, with the processor operable to perform calculations and recordings using the outputs to determine at least one attribute of the movement of the test subject. Preferably, the transducers are selected from the group consisting of force and pressure transducers, with the former being most preferred. The preferred force transducers must be capable of measuring both static and dynamic forces.

With this force plate actometer, it is possible to determine on a real time basis the variation in location and/or magnitude of the force exerted by the subject on the plate. With this knowledge, it is possible, through use of appropriate processor software, to determine and/or quantify a variety of attributes of the movement of the test subject. Thus, attributes selected from the group consisting of the position of the subject on the plate, distance traveled by the subject over a defined period of time, the angle and direction of rotation of movement, a spatial statistic of the movement of the subject, stereotypies, tremor and wall rearing can be accurately measured. Furthermore, this can be accomplished without the need for human or video camera monitoring of the test.

In preferred forms, the overall force plate actometer includes a rigidly mounted enclosure for confining the test subject to a predefined region of the force plate. This enclosure is spaced slightly above the force plate but is supported to prevent displacement thereof by a test animal. The enclosure may be any desired shape, but usually square or circular in plan enclosures are used.

As indicated, the force plate actometer is capable of performing real time calculations. The results of these real time calculations are stored and are used in post-test period calculations to develop further locomotor and/or motion information about the test animal. During the course of the tests, the processor repeatedly performs an initial set of calculations, with the interval between successive calculations being up to about 1 second, and more preferably from about 0.01–0.1 seconds.

The force plate actometer can thus be used to perform a variety of animal study tests. Besides those mentioned previously, the device can quantify the motor concomitants of drug-induced seizures; can count and quantify the intensity of vertical jumps (as in the "popping" behavior induced in mice by NMDA antagonists such as MK-801) and the spatial location of such jumps; can measure total energy expenditure due to movement during a test period; when fitted with proper attachments, it can be used to develop automated y mazes, t mazes or radial mazes for mouse or rat studies of learning (discrimination learning, discrimination reversal learning, spatial learning, and working memory); be adapted to acoustic startle paradigms (such as the prepulse inhibition paradigm, thought to yield information about some of the neurological mechanisms of schizophrenia and other psychopathologies); and can be incorporated into the floor of an operant chamber to provide descriptions of animal behavior both during bouts of lever pressing and when lever pressing is not occurring.

DETAILED DESCRIPTION OF THE PREFERRED EMBODIMENT

Construction of the Preferred Force Actometer

Figures 1, 2:
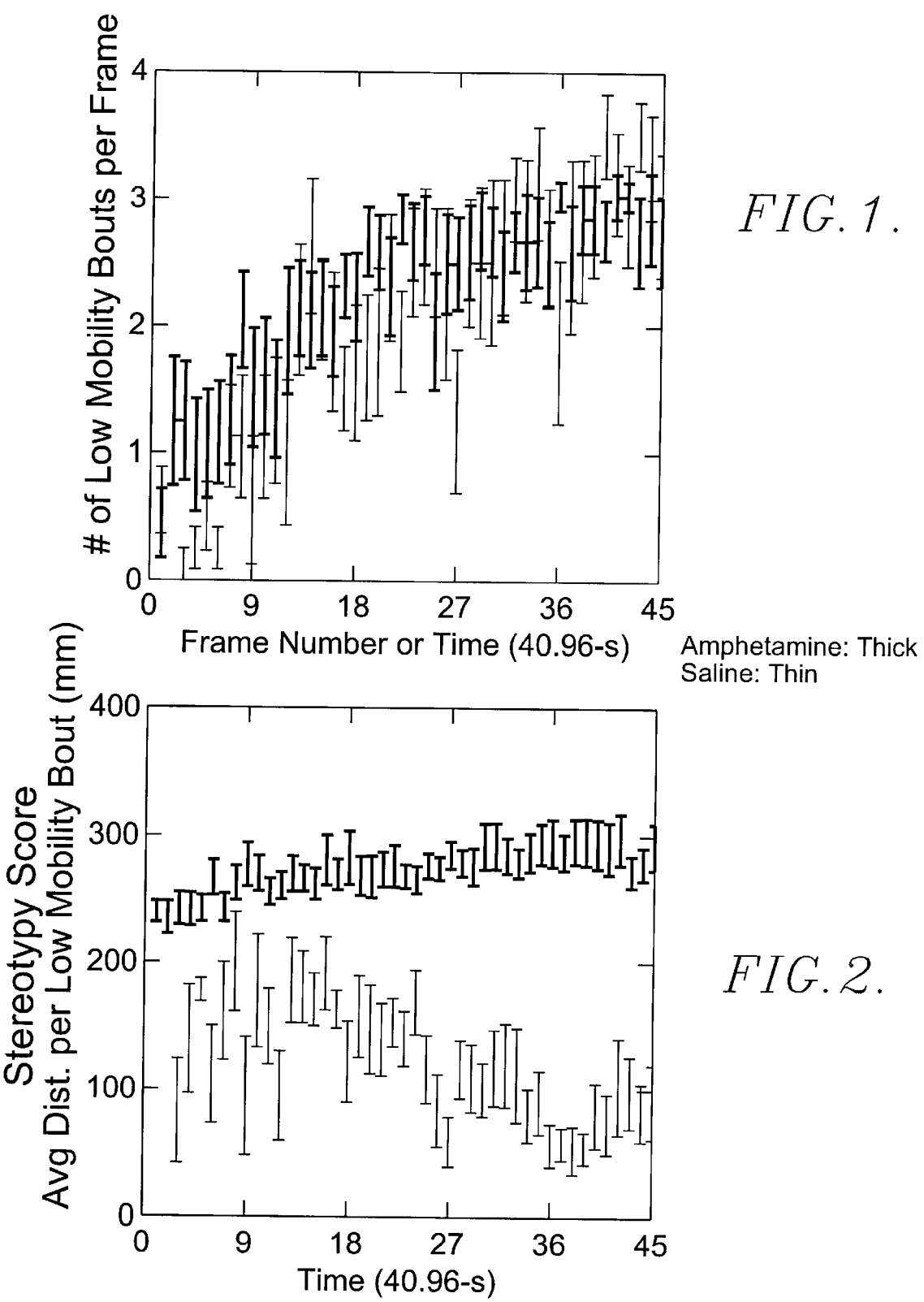
FIG. 1 is a graph illustrating the number of low mobility bouts per frame versus frame number or time for an amphetamine-treated rat and a control rat, using the force plate actometer of the invention and as described in Example 1.
FIG. 2 is a graph of stereotypy score versus time for the amphetamine-treated and control rats as described in Example 1.

FIGS. 20–24l depict a preferred force plate actometer 30. Broadly speaking, the actometer 30 includes a force plate 32, a transducer assembly 34, a support assembly 36, and a test subject enclosure 38. In addition, a computer 40 is operatively coupled with the transducer assembly 34 to perform real time and offline calculations.

In more detail, the force plate 32 includes a foam core art board (4.8 mm thick) panel 42 painted with blank urethane and faced on the sensing side with 0.15 mm thick aluminum foil 44 (GoodFellow Product No. AL000601, Hard Temper). The foil 44 is glued to the foam core board with a spray coating of rubber-based adhesive, and a depending tape skirt 45 is applied about the periphery of the panel 42. In the form illustrated, the force plate presents a 305 mm square perimeter and a 280 mm square sensing region. The mass of the force plate is 105 g. The stiffness of the force plate is measured by placing the plate in position onto the transducer sensing shafts, so it is suspended at the four points that form a 280 mm square. A 5 mm square piece of double sided picture mounting adhesive tape (1 mm thick) attaches the plate to each transducer shaft. The transducer shafts that support the plate are fitted with a threaded collar that provides a support shaft diameter of 5 mm (too small a diameter would result in too much pressure on the foam core board and may cause puncture of the surface when large rats are used as subjects). With the plate so suspended the amount of bending of the plate under load is measured. The load is a class C calibration weight positioned at the center of the plate upper surface. Bending under load is measured at a point along one side of the plate half way between two support points. With a 50 g weight, no discernable downward deflection was detected (less than 0.1 mm). A 500 g weight produced a deflection of 1.0 mm.

An alternate plate using composite materials (aluminum foil and aluminum honey comb) has also been fabricated.

This plate is of lower mass (about 65 g) and is stiffer (deflection under 500 g load estimated to be about 0.1 mm). The materials are one piece of 0.125 mm thick aluminum foil 300×300 mm weighing 30.4 g, a second piece of this foil with a substantial portion cut away to yield a specially shaped under piece weighing 15.7 g, and a piece of 300×300 mm aluminum honeycomb (Good-Fellow AL002960, 5 mm thick) weighing 13.1 g. The honey comb is sandwiched between the upper continuous piece of foil and the lower cut out piece of foil and spot glued together with epoxy.

Figure 23:
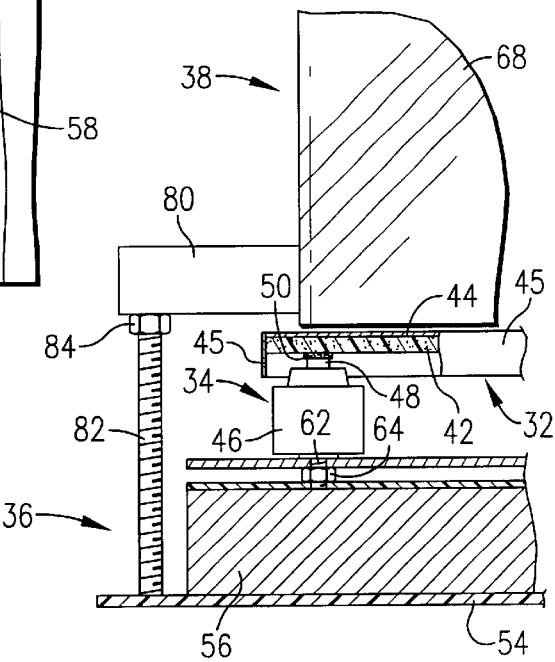
FIG. 23 is a fragmentary view in vertical section illustrating the connection between the force transducers and force plate of the actometer apparatus.

The transducer assembly 34 includes four individual force transducers 46 having shaft centers located at the four corners of the sensing square of force plate 32. As illustrated in FIG. 23, the shaft 48 of each transducer 46 is secured to the underside of panel 42 by means of double faced tape 50. The transducers in the preferred embodiment are Model 31 "Precision Miniature Load Cells" manufactured by Sensotec of Columbus, Ohio. The sensors have the following characteristics: Range: 250 g; deflection under max load: 0.0025 inches (practically isometric); natural frequency unloaded: >200 Hz; amplifier/conditioner: Sensotec Model UV (BE124) Universal Vehicle In-line Amplifier; nonlinearity: +/−0.15% full scale; and output: 20 mv/v.

Figure 21:
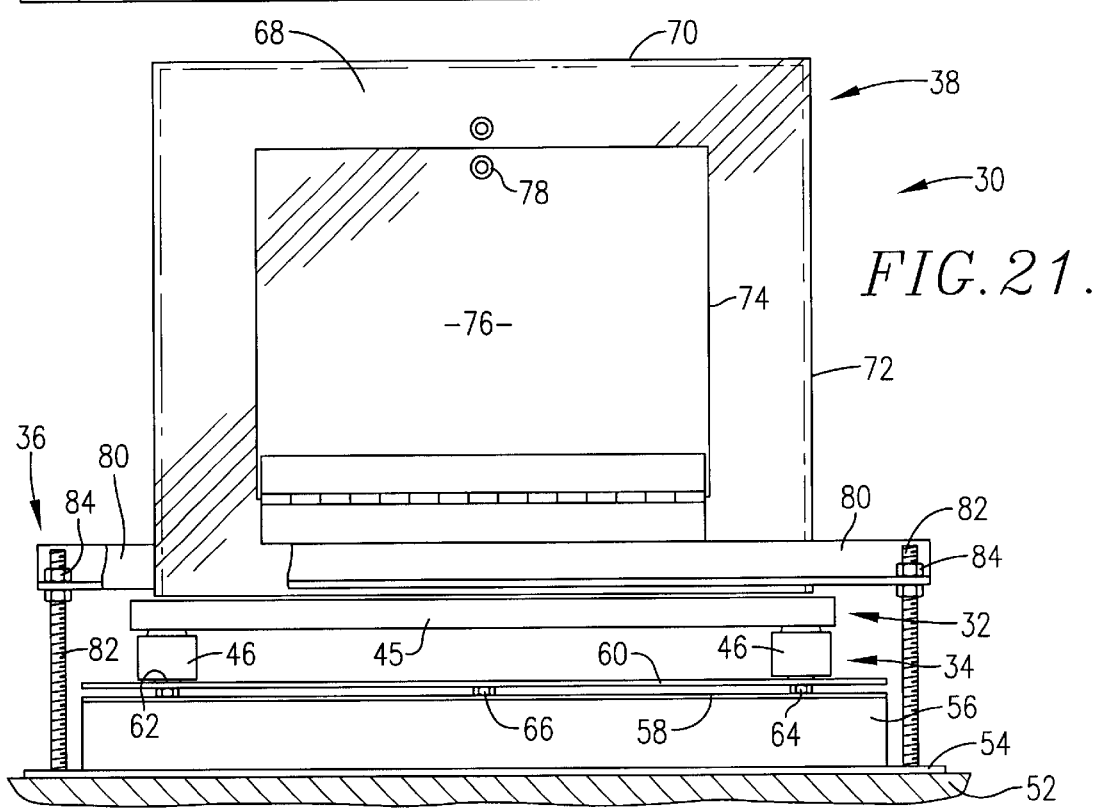
FIG. 21 is a front view of the force plate actometer apparatus.
Figure 24:
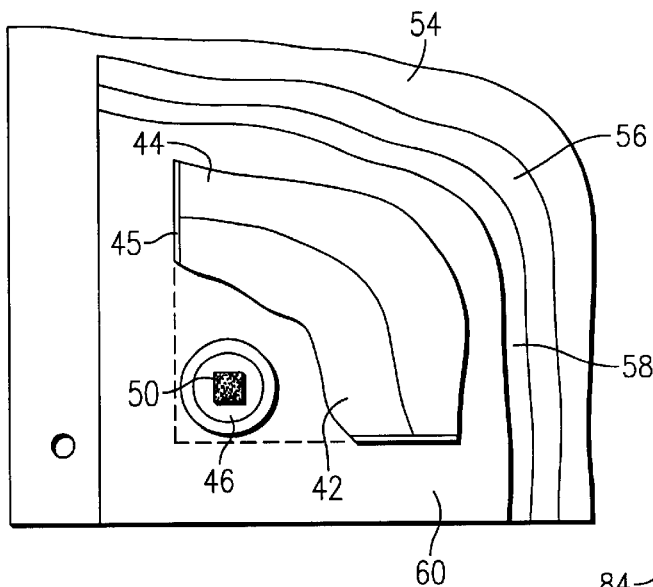
FIG. 24 is a top view with portions broken away illustrating the various components of the force plate, transducers and support assembly of the actometer apparatus.
Figure 22:
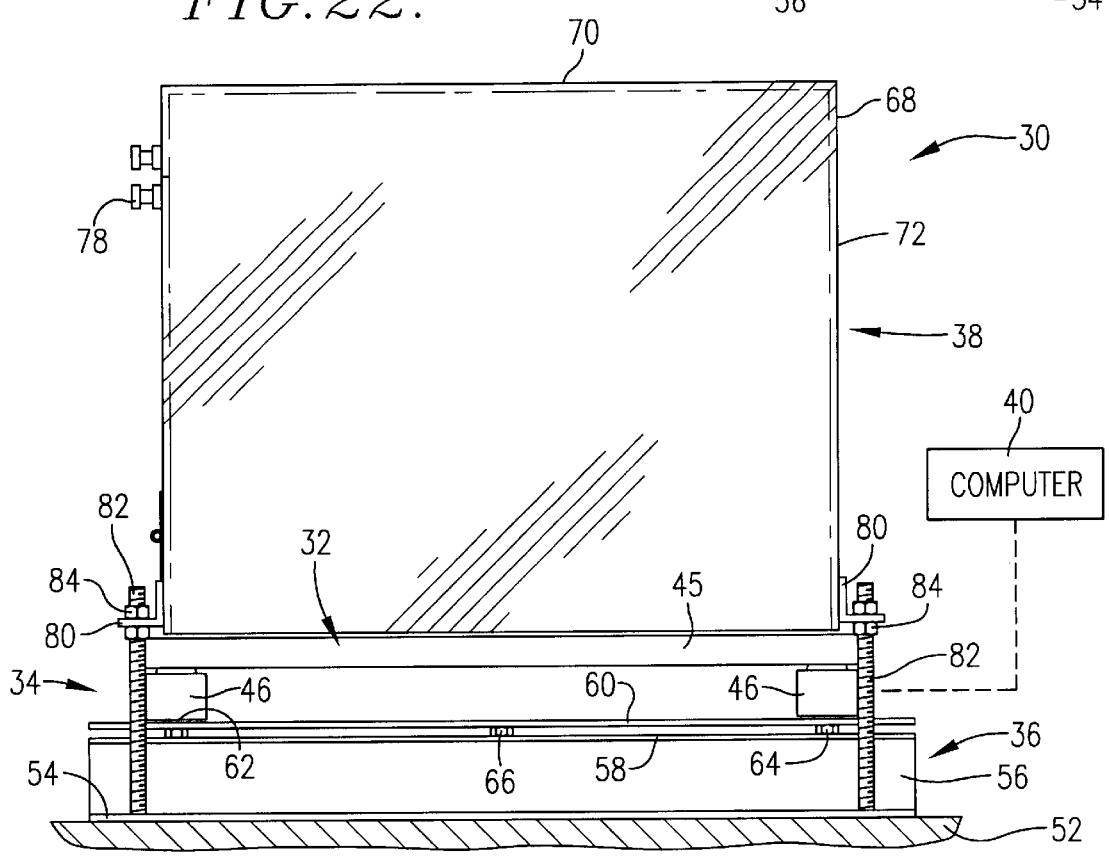
FIG. 22 is a side view of the force plate actometer apparatus.

The support assembly 36 includes a base 52, a chamber locator plate 54, a ballast plate 56, a locator plate 58 for the reference plate, and a reference plate 60. These components are in superposed relationship as best seen in FIGS. 21 and 22.

The base 52 can be any large, rigid structure. Good results have been obtained by using a sound attenuating cubicle, whose door is kept closed during test sessions. The chamber locator plate 54 is in the form of a ⅛ inch thick Plexiglas (349×500 mm) plate having four holes drilled in it to provide for reproducible positioning of the chamber 38 as will be described.

The ballast plate 56 is a piece of granite (349×349×28.6 mm) weighing 8.92 kg. Its purpose is to provide a degree of mechanical isolation between the force plate and the surrounding environment so that vibrations due to people walking by are not picked up by the sensors. The ballast plate rests on four 1 in square pieces of foam rubber ½ inch thick (the foam is of a density used in furniture manufacture). The position of the ballast plate must marked on the chamber locator plate so that it can be reproducibly repositioned (less than 0.5 mm error) after it has been removed for cleaning.

The locator plate 58 is a 349×349 square plate of ⅛ inch thick Plexiglas plate whose purpose is to form a template with four holes to receive the transducer mounting shafts (which are centered on the sensing shafts) so that the reference plate and transducers can always be precisely repositioned after removal for cleaning or transducer replacement. Accurate positioning is important because the sensing surface of the force plate should be under the chamber such that the inside corners of the chamber align with the center of the transducer shafts. The locator plate is glued to the ballast plate with silicone cement.

Reference plate 60 mechanically fixes the position of the transducers with respect to one another forming a 280 mm square with the center of the transducers located at the corners of the square. The reference plate is stainless steel because this material is resistant to the corrosive effects of animal urine and feces. The plate is about 1 mm thick and is a square 349×349 mm on a side. Referring to FIGS. 21 and 22, it will be seen that the openings in reference plate 60 receive the depending transducer mounting shafts 62, the latter being secured to the plate 60 by nuts 64. A center spacer nut 66 is also positioned between the reference plate 60 and locator plate 58.

The enclosure 38 includes an upstanding, square in plan Plexiglas housing 68 having a top wall 70 and depending sidewalls 72, one of which is cut out to present an access opening 74. The opening 74 is normally closed by a Plexiglas door 76 which is hingedly secured to the housing 68 and equipped with a handle 78.

The housing 68 is constructed from Plexiglas so that it is transparent and allows visual observation of a subject during the recording session if desired. The preferred enclosure is a cube 280 mm on a side (inside dimensions). The height is needed to accommodate rats so that they may engage in the full range of upward rearing during exploratory behavior. Ventilation holes are drilled in the top of the chamber but these are out of reach for nose poking by either rats or mice. The interior of the enclosure should be smooth and free of protrusions (such as bolt heads and shafts). Uniformity of surface, as much as possible, is the rule since distinctive features may bias the animals' use of space in the chamber. Some strains of mice exhibit pronounced tendencies to climb and the smooth interior surfaces of the enclosure prevent climbing. The Plexiglas is held together with adhesive joints along the edges of each piece. Preferably, the precision of manufacture of the enclosure should allow for no more than 1 mm error because the positioning of the chamber above the force plate 32 is what ensures that the coordinate system, used by the computer to measure the animal's position, faithfully represents the behavior of the animal.

The enclosure 38 is suspended above (2 mm) the force plate itself so that the only load on the plate is the animal subject. This mechanical separation between the plate and the chamber makes possible the detection and quantification of wall rearing. The mass of the chambers must be sufficient to prevent the animals' wall-directed behaviors from moving the chamber out of its proper position for recording. The enclosure is easily removed and replaced in order to afford convenient access for removing fecal boli from the chamber between sessions.

The enclosure 38 is supported above force plate 32 by means of a pair of brass connector bars 80 attached to the lower margins of two opposed sidewalls 72 by conventional fasteners. The bars 80 are in turn supported by four corner-mounted, threaded legs 82, secured in place by nuts 84. In order to obtain the desired reproducible positioning of the enclosure 38, the lower ends of the legs 82 fit within the previously mentioned openings provided in chamber locator plate 54.

In certain animal testing protocols, rotometers are used to quantify a test animal's response to drugs. For example, by scientific convention circular rotometers are used to study the unilaterally 6-hydroxydopamine lesioned rat (most common rodent model of Parkinson's disease). To quantify the lesioned animal's response to apomorphine or amphetamine (and many other drugs) an insert 86 (see FIG. 20) is employed within the enclosure 38 which transforms it into a cylindrical enclosure. This enclosure has a door 88 that allows it to be opened through the door 76 of enclosure 38 for placing the subject in and retrieving it from the circular chamber. The insert 86 is made of Plexiglas and is bolted to the top of enclosure 38 by means of L-brackets 90 and screws 92, so that the center of the cylindrical space is centered on the force plate coordinate center (i.e., x=0 mm, y=0 mm). The bottom edge of the cylinder is suspended above the force plate sensing surface. The test animals are free to move within the insert 86 and this feature usually increases sensitivity to movement-related drug or brain manipulations.

Calibration of the actometer 30 can be divided into three parts: force transducers, distance, rotation.

The force transducers are calibrated individually by placing static weights on the sensing shaft. During this process a calibration program displays the numerical values of the transducer output expressed in units provided by the A/D converter. Gain and zero are manipulated until 1 g equals 3 A/D units. The gain value is based on empirical experience. It represents a practical compromise between sensitivity and range. After each transducer is so calibrated, the force plate is attached to the transducers. The Zero point is adjusted using the control on the amplifier conditioner until all 4 transducers read zero. Then a 100 gram weight is applied to the force plate and a 300 unit reading is obtained from the sum of the 4 transducers outputs.

In the preferred force actometer 30, distance is derived from the variations of the force transducers with a moving load on the force plate. Because of the sensitivity of the actometer 30, minute variations in force can cumulate distance traveled. However, in order to serve as a successful measurement instrument, these smaller variations can be averaged out. In practice the distance comparisons are between experimental conditions (e.g., between a group of animals receiving a treatment and a group of animals serving as untreated controls). A moving average smooth of 5 is employed to obtain the distance traveled in mm. This selection was based on empirical studies of the behavior of the preferred force plate 32 under static load, and when a human finger tip (low vibration resembling animal movement albeit on only "one foot") traced a circle of known diameter drawn on the force plate. The table below gives data for 7 frames of 40.96 s each of finger tracing a circle with a circumference equal to 0.5 meters (500 mm). The Pearson correlation between recorded and predicted distance (column 2 and column 4 in the table) was +0.999. The means are also in agreement. The finger tracing calibration shows that the distance measurements are veridical.

Table of results from the finger tracing distance calibration:

| Time Frame | Distance Recorded (m) | Rotations/frame | Predicted Distance (m) |
| --- | --- | --- | --- |
| 1 | 3.824 | 7.60 | 3.800 |
| 2 | 3.270 | 6.57 | 3.290 |
| 3 | 3.138 | 6.33 | 3.170 |
| 4 | 3.402 | 6.86 | 3.430 |
| 5 | 3.375 | 6.80 | 3.400 |
| 6 | 3.126 | 6.27 | 3.140 |
| 7 | 3.363 | 6.78 | 3.390 |
| Means: | 3.357 | 6.74 | 3.374 |

The rotation calibration is accomplished with a calibrator apparatus that uses a 6 rpm synchronous motor with a beam attached to the motor shaft. Clamps are used to position the motor and beam (beam length is effectively about 10 cm) a short distance above the force plate 32. A length of surgical gauze is taped to the beam and a 50-g calibration weight is placed on the gauze. When the motor is activated, the beam drags the weight in a circular arc around the plate. The exact length of a nominal 30-min recording session is 1843.2 s or 30.72 min. At 6 rpm the expected number of rotation is 6×30.72, or 184.32 rotations. The obtained value of an actual run of the calibrator on the instrument was +184.28 rotations. This is an error of about 0.02%. The "+" indicated that the movement was in the counter clockwise direction, which is consistent with the direction of movement of the weight that was dragged around the plate.

Sample Calculations

Figure 25:
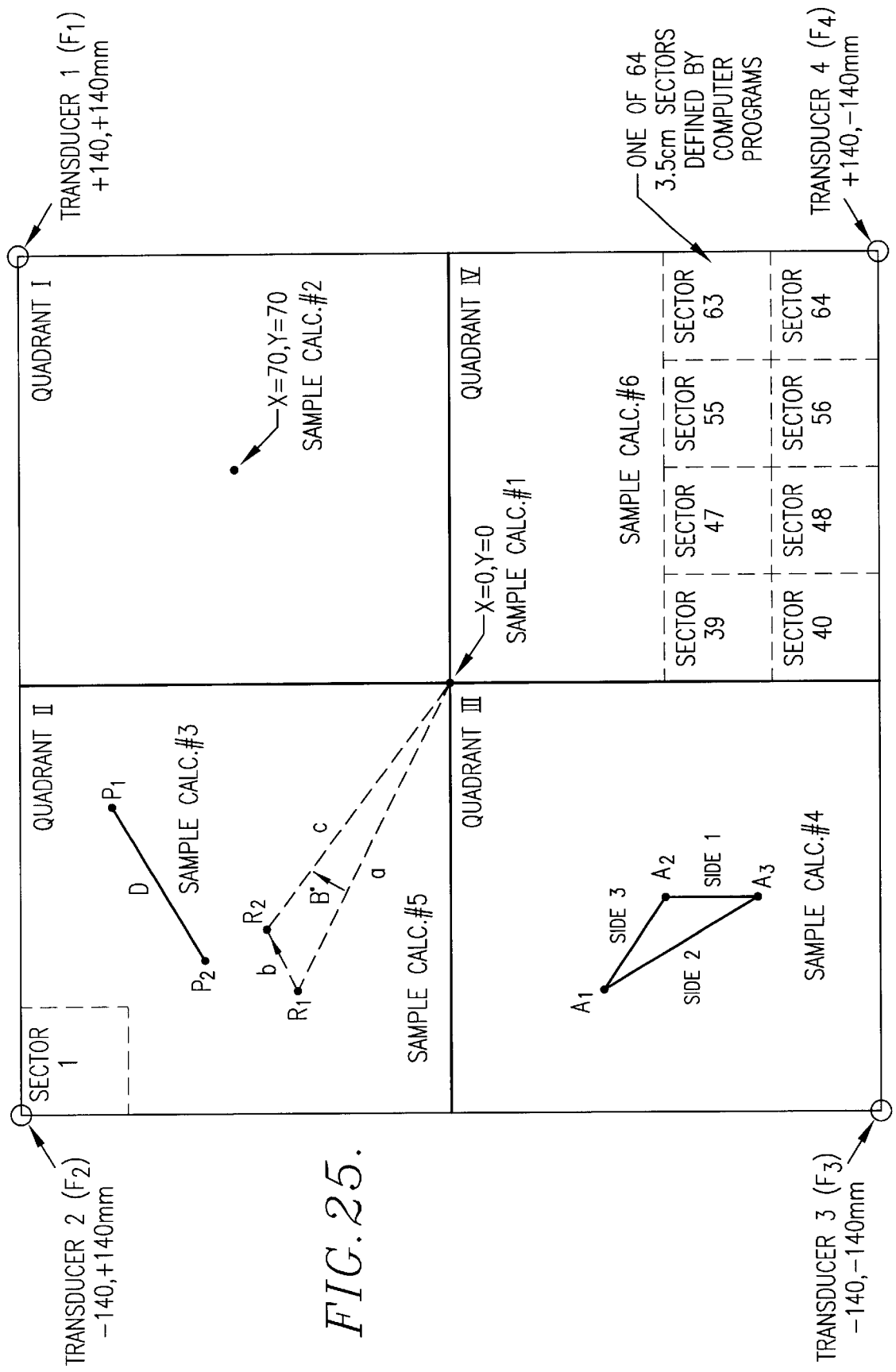
FIG. 25 is a schematic plan view of the force plate of the actometer apparatus shown with the coordinate system of the preferred embodiment applied to the plate and with exemplary illustrations of various calculations which can be performed using the actometer apparatus, as explained in Sample Calculations Nos. 1–6.

FIG. 25 sets forth in schematic form the layout of the force plate 32 of the actometer 30, with a coordinate system applied. The 0,0 origin is at the center of the plate as shown, whereas the four transducers are located at the corners. With this quadrant layout, calculations can be performed to ascertain the position of a body within the coordinate system, the distance between points, the area defined by three successive points, angle and direction of rotation with respect to the origin, and other useful information. In practice, the computer 40 is loaded with a program (explained in detail hereafter) to calculate the desired values. However, the following sample calculations are provided which explain the preferred algorithms used in the program.

Sample Calculation No. 1

In this example, a 100 g weight is placed at the origin. The transducers 1–4 read $F_1$=25 g, $F_2$=25 g, $F_3$=25 g, and $F_4$=25 g. The X,Y coordinates of the position of the weight are:

$$X = (X_1 F_1 + X_2 F_2 + X_3 F_3 + X_4 F_4)/(F_1 + F_2 + F_3 + F_4)$$

$$Y = (Y_1 F_1 + Y_2 F_2 + Y_3 F_3 + Y_4 F_4)/(F_1 + F_2 + F_3 + F_4)$$

where the force values are set forth above and $X_1$=140 mm, $Y_1$=140 mm, $X_2$=−140 mm, $Y_2$=140 mm, $X_3$=−140 mm, $Y_3$=−140 mm, $X_4$=140 mm, and $Y_4$=−140 mm.

Using these values, the X and Y coordinates are calculated to be 0,0.

Sample Calculation No. 2

In this example, a 100 g weight is placed on the plate at the position shown in quadrant I. The transducer values are $F_1$=60, $F_2$=15, $F_3$=10, and $F_4$=15. Using the formula of Calculation No. 1, the position of the weight is determined to be X=70, Y=70.

Sample Calculation No. 3

In this example, the distance D between two points $P_1$ and $P_2$ in quadrant II is determined. The coordinates of $P_1$ are $X_1$=−40, $Y_1$=110 and $P_2$ are $X_2$=−90, $Y_2$=80. Using the formula:

$$D = \sqrt{(X_1 - X_2)^2 + (Y_1 - Y_2)^2}$$

the distance is calculated to be 58.3 mm.

Sample Calculation No. 4

In this example, the area of a triangle formed by three successive points shown in quadrant III is calculated. The coordinates are: $A_1$, $X_1$=−100, $Y_1$=−50; $A_2$, $X_2$=−70, $Y_2$=−70; and $A_3$, $X_3$=−70, $Y_3$=−100. Using the technique shown in Calculation No. 3, the sides of the triangle are calculated to be: side 1=30.0, side 2=58.3, side 3=36.1. Using Heron's Formula for the area of a triangle, the area is calculated to be 451.5 $mm^2$.

Sample Calculation No. 5

In this example, the angle and direction of rotation with respect to the origin are determined, using the points shown in quadrant II. The coordinates are: origin, $X_1$=0, $Y_1$=0; $R_1$, $X_2$=−100, $Y_2$=50; and $R_2$, $X_3$=−80, $Y_3$=60. First, the lengths of the sides of the triangle with one vertex at the origin are calculated using the technique of Calculation No. 3, i.e., side a=111.80, side b=22.36 and side c=100.00.

The direction of rotation is determined by the formula:

Direction=$(X_2-X_1)\cdot(Y_3-Y_2)-(Y_2-Y_1)\cdot(X_3-X_2)$

In this case, the result is −2000, confirming that rotation is to the right as shown in FIG. 25. (The magnitude is not meaningful because the motion was in a two-dimensional plane.)

The angle B is determined using the law of cosines:

Cos $B=(a^2+c^2-b^2)/2ac$

Applying this formula, the angle with direction is calculated to be −10.33°.

Sample Calculation No. 6

In this example, a spatial statistic is determined, which is a measurement of how a subject uses space. In order to perform this calculation, the plate as shown in FIG. 25 is divided into 64 equal area sectors. The aim of the calculation is to derive a value relative to a theoretical subject which would evenly visit each sector during a test.

The following sector grid is an example of a subject "running around" the force actometer, traversing a number of the individual sectors. The bolded values represent the distance traveled by the subject in the sectors during the test period.

| 1 | 9 | 17 | 25 | 33 | 41 | 49 | 57 |
|---|---|---|---|---|---|---|---|
|   | 160 | 170 | 150 | 20 |   |   |   |
| 2 | 10 | 18 | 26 | 34 | 42 | 50 | 58 |
|   | 155 |   |   |   | 60 | 90 |   |
| 3 | 11 | 19 | 27 | 35 | 43 | 51 | 59 |
|   | 165 |   |   |   |   | 175 |   |
| 4 | 12 | 20 | 28 | 36 | 44 | 52 | 60 |
|   | 185 |   |   |   |   | 170 |   |
| 5 | 13 | 21 | 29 | 37 | 45 | 53 | 61 |
|   | 190 |   |   |   |   | 150 |   |
| 6 | 14 | 22 | 30 | 38 | 46 | 54 | 62 |
|   | 170 |   |   |   |   | 120 |   |
| 7 | 15 | 23 | 31 | 39 | 47 | 55 | 63 |
|   | 70 | 80 | 150 | 175 | 170 | 100 |   |
| 8 | 16 | 24 | 32 | 40 | 48 | 56 | 64 |

The sum of the distances in the above grid is 2875. Each of the individual sector values is expressed as a percentage of the 2875 total, and a difference calculation is made between each percentage and the theoretical percentage for a situation where the subject travels an equal distance through each sector. These differences are then squared, summed, and the square root of the summed value is obtained as a spatial statistic. In the above example, the statistic was $(375.259)^{1/2}=19.372$.

As a comparison, an example calculation is made where the subject stayed in one sector throughout the test period. This grid is shown below.

| 1 | 9 | 17 | 25 | 33 | 41 | 49 | 57 |
|---|---|---|---|---|---|---|---|
| 2 | 10 | 18 | 26 | 34 | 42 | 50 | 58 |
| 3 | 11 | 19 | 27 | 35 | 43 | 51 | 59 |
| 4 | 12 | 20 | 28 | 36 | 44 | 52 | 60 |
| 5 | 13 | 21 | 29 | 37 | 45 | 53 | 61 |
| 6 | 14 | 22 | 30 | 38 | 46 | 54 | 62 |
| 7 | 15 | 23 | 31 | 39 | 47 | 55 | 63 |
|   |   |   |   |   |   | 2875 |   |
| 8 | 16 | 24 | 32 | 40 | 48 | 56 | 64 |

The spatial statistic derived from this example was $(9843.750)^{1/2}=99.216$.

The minimum possible value in this calculation is 0.0, and the maximum value is 99.216, with the 64 sectors. The larger the discrepancy from uniform, the larger the statistic.

Preferred Software

In practice, four of the actometers 30 are operated simultaneously via the computer 40 (which is typically a conventional PC), so as to provide more statistically significant results. Therefore, the ensuing discussion of software will assume that four actometers are coupled to the computer 40 for simultaneous testing purposes. In addition, two separate programs are described, namely the 4PLATES.PAS program which is a program which collects data in real time during testing, and OFFLINEP.PAS, which uses the recorded data to calculate additional values. Flow diagrams for the two programs are provided in FIGS. 19A and 19B (4PLATES PAS) and FIGS. 18A, 18B and 18C (OFFLINEP.PAS).

Figure 19A:
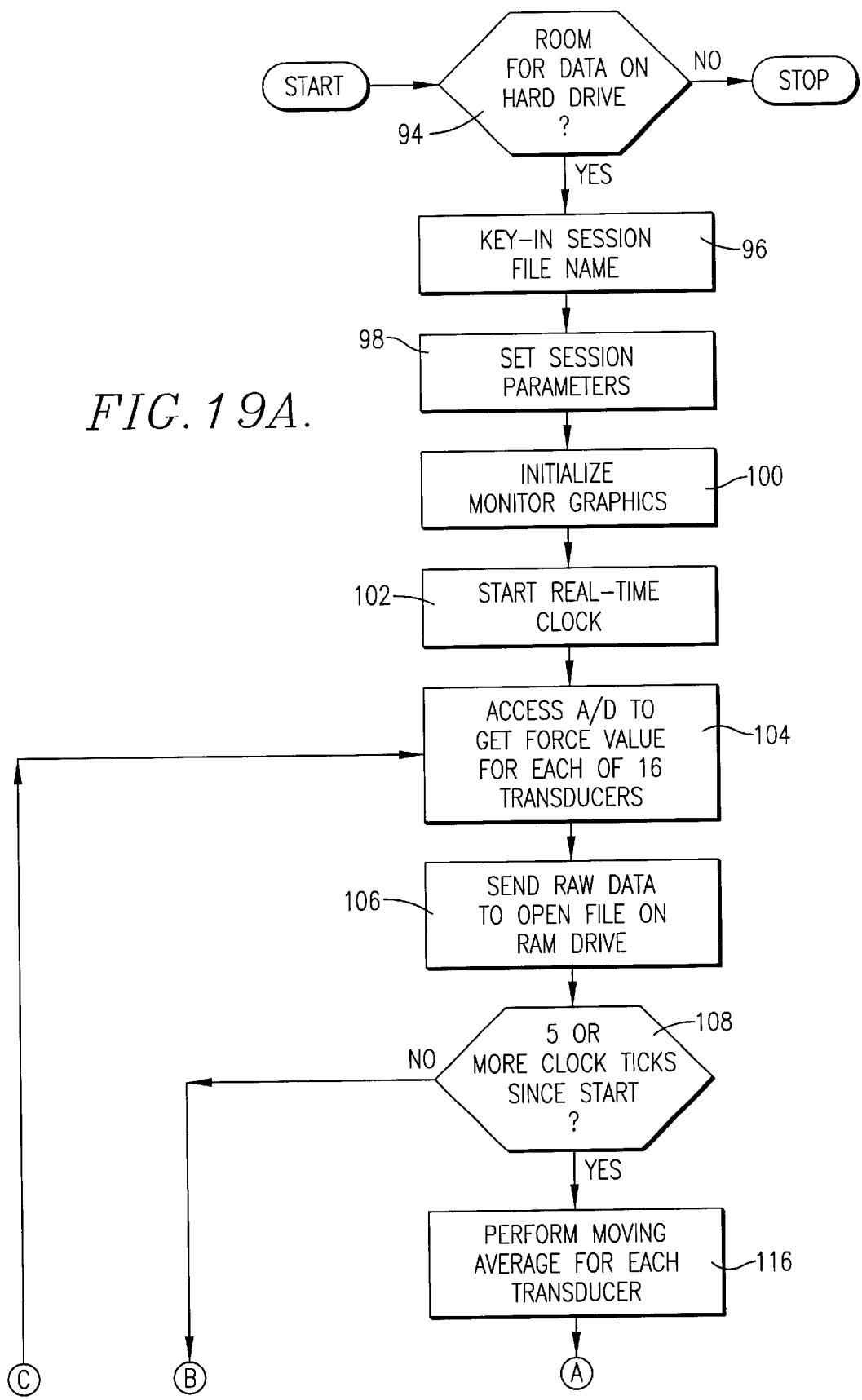
FIG. 19A is a portion of a flow diagram of another preferred software program used in the invention, 4PLATES.PAS.
Figure 19B:
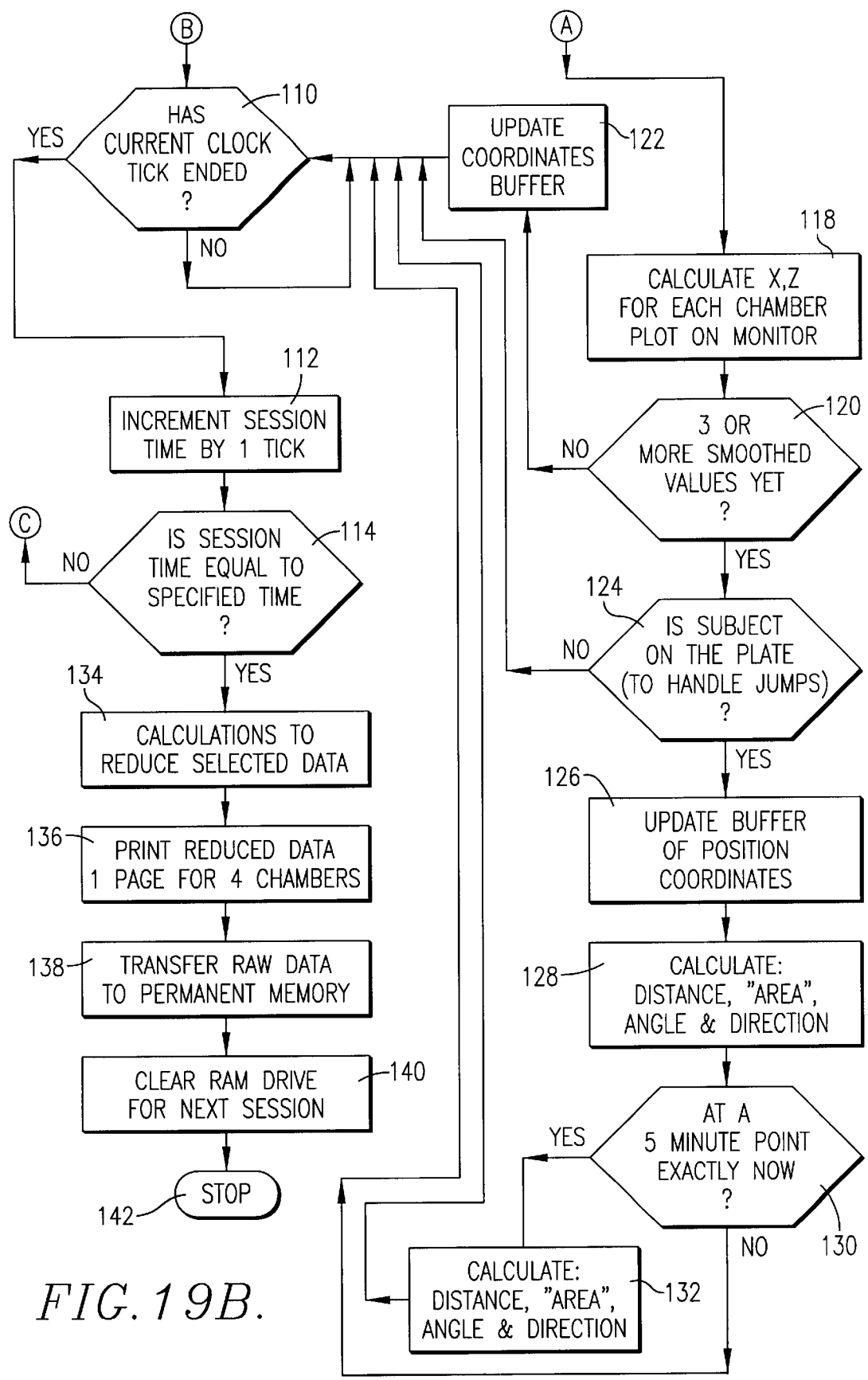
FIG. 19B is a continuation of the flow diagram of FIG. 19A.

Turning first to FIGS. 19A and 19B, it will be assumed that animal subjects are placed within the enclosures 38 (or within inserts 86 if such are used) under appropriate conditions for the desired test. The 4PLATES.PAS program is then started (FIG. 19A). The first step 94 is a hard drive check to insure that there is sufficient room for the anticipated data. If this check is successful, the program moves to step 96 where the session file name is entered. Thereafter, in step 98 the session parameters are set.

These parameters are dictated by the physical characteristics of the force plate 32 and are assigned values before the real-time loops are started. The positions of each of the four force transducers 46 are defined by the fixed locations of the transducer that are bolted to the plate 60. For transducer 1, the location of the transducer is in quadrant I (see FIG. 25) at x=140 mm and y=140 mm; for transducer 2 in quadrant II: x=−140 mm, y=140 mm; for transducer 3 in quadrant III: x=−140 mm, y=−140 mm; for transducer 4 in quadrant IV: x=140 mm, y=−140 mm.

In Pascal code this is expressed as:

$X[1]:=140.0; X[2]:=31\ 140.0; X[3]:=-140,0; X[4]:=140.0;$ $Y[1]:=140.0; Y[2]:=140.0; Y[3]:=-140.0; Y[4]:=-140.0;$

The gain of the force transducers is selected so that 3 units of data read by the A/D converter is equal to 1.0 gram equivalent weight. Thus the force unit used in the program calculations is 0.33 gram equivalent weights. Gram derived units are used instead of Newtons because gram weights are used in the calibration procedure, and animals' body weights are most commonly expressed in gram weight units. Distance units used by the program are mm. Thus output is expressed in mm and 0.33 gram equivalent weights.

In order to provide feedback during the session on the computer monitor and in the form of printed output at the end of each session, several quantities are calculated online. These are: 1) the proportion of the session time spent in the 64 separate 3.5 cm square sectors of the force plate. This gives an indication of the degree to which the behavior of the animal is distributed in space across the session. 2) the mean Fz force for the session. This measure will be the animals' body weight in grams multiplied by 3.3) the Fz variance. This measure is the variance (root mean square of the variation in the sum of the forces on the 4 transducers of each actometer 30) across the session. The session time is actually 92160×0.02 s=1843.2 s. This value was chosen to so as to provide 45 subepochs of 40.96 s each (or 2048 samples), which provides a convenient power of two multiple for a series length to be processed by Tukey-Cooley Fast Fourier Transform. 4) distance traveled in mm, which is basically the line integral of movement of the center of force; 5) the "area" measure, which is borrowed from human postural sway analyses and yields a number that increases in relation to the number of sharp turns instead of straight-line runs; 6) number and direction of net rotations where a negative sign indicates rotation to the right (clockwise as seen from the top of the chamber looking down on the animal) and no sign (positive) indicates turns to the left. 7) distance traveled is also automatically calculated by 5-min intervals so that habituation phenomena can be easily seen across the 30-min session.

The data acquisition program must set up arrays and registers to calculate these quantities in real time so they are ready for printing at the end of the session and so the monitor can display the position of the test subjects in real time.

The Pascal code for initializing the various arrays is given by:

OneMin:=3072; {3072 is nominally 1 min minute at 50 samples/s/transducer}
NumMin:=30; {set number of minutes here; 30 min is nominally 92160 samples}
SessionTime:=OneMin*NumMin;
PassNo:=0;{used in DisplayXY to control buffer filling for smoothed coordinates}
DefineSectorTable; {sets up array space for the 64 3.5 cm sectors of the force plate}
For Ix:=1 to 4 Do
  Begin
  Xc[Ix,1]:=0.0; Xc[Ix,2]:=0.0;pXc[Ix]:=0.0;
  Yc[Ix,1]:=0.0; Yc[Ix,2]:=0.0;pYc[Ix]:=0.0;
  Fsum[Ix]:=0.0;
  GlobalDistance[Ix]:=0.0;
  GlobalArea[Ix]:=0.0;
  Distance[Ix]:=0.0;
  Area[Ix]:=0.0;
  For Ixx:=1 to 6 Do Dby5[Ixx,Ix]:=0.0;
  FSumSqr[Ix]:=0.0;
  FSumForMean[Ix]:=0.0;
  NumLeft[Ix]:=0.0; NumRight[Ix]:=0.0;
  LeftMeanAngle[Ix]:=0.0; RMeanAngle[Ix]:=0.0;
  End;

Once the parameters are set, the monitor is initialized in step 100 and the real time clock is started in step 102. At this point, data is acquired by accessing the A/D converter to obtain force values for each of the 16 transducers (step 104). This raw data is sent to an open RAM file (step 106). Next, the program determines whether five or more clock ticks have elapsed since the start (step 108). If the answer to this query is "NO", the program advances to step 110 (FIG. 19B) where a determination is made of whether the current clock tick has ended. If the determination is "NO", the program loops until the tick has ended. When a "YES" is determined, the program moves to step 112 and then to step 114 to determine whether the session time is equal to the specified time. If the answer is "NO", the program loops back to step 104 of FIG. 19A, to repeat steps 106 and 108 until a "YES" is determined.

Once the step 108 "YES" is obtained, the program advances to step 116 to perform a moving average calculation for each transducer. X, Y values for each actometer plot are calculated in step 118, whereupon the program advances to step 120. In this step a determination is made whether three or more smoothed values have been obtained. If the answer is "NO", the program updates the coordinates buffer in step 122, and advances through the previously described loop defined by steps 110–114 back to step 104.

When a "YES" answer is obtained at step 120, the program next moves to step 124 to determine whether the test subject is on the plate. This step is inserted to handle situations where the test animal may be jumping. If the answer is "NO", the program returns to the loop of steps 110–114 and back to step 104. If the answer is "YES", the program updates the buffer of position coordinates in step 126 and then calculates, distance, area, angle of rotation and direction of rotation in step 128.

Distance, area, and rotation (and it's direction) are calculated after the moving average smooth has been applied to the data from each transducer. The averaging kernel is 5 (i.e., the number of successive values used in calculating the smooth value is 5). The smoothing is performed to reduce the effect of electrical noise in the transducers and to reduce the effect of relatively high frequency variations in force caused by different feet striking the force plate at measurably different times. The value of 5 for the moving average was determined by empirical studies with rats and mice. All frequency information available from the 50 Hz signals is recovered in the Fourier analysis performed offline on the recorded raw data that is not smoothed. The smoothed force values are used to calculate the coordinates (X,Y) of the point representing the location of the center of force of the animal on the force plate.

Distance is simply defined as the distance that the center of force moved between $(X_1, Y_1)$ and $(X_2, Y_2)$, i.e., between time point 1 and time point 2 occurring 0.02 s later. Then these distances are integrated across time to yield total distance traveled. The calculation of the distance D between two points defined by $X_1$, $Y_1$ and $X_2$, $Y_2$ in Cartesian coordinates is shown in Sample Calculation No. 3.

In Pascal code the distance calculation is:

For Ib:=1 to 4 Do {do it once for each chamber}
  Distance [Ib]:=SQRT(Sqr(XcBuf[2,Ib]−XcBuf[3,Ib])+ Sqr(YcBuf[2,Ib]−YcBuf[3,Ib]));
For Ib:=1 to 4 Do
  GlobalDistance[Ib]:=GlobalDistance[Ib]+Distance [Ib]; {sum the result, i.e, integrate}

The area measure is the area of the triangle formed by three successive locations of center of force (i.e., three points defined by three successive clock ticks of 0.02 s each). If the three coordinates form a straight line, then no calculation is performed. As three points in a plane define a triangle, the coordinates of the three points are used to calculate the length of each side using the distance algorithm. Then the area of the triangle is calculated by using the general formula for the area of any triangle (Heron's formula; see Sample Calculation No. 4).

In Pascal code the area calculation is:

For Ib:=1 to 4 Do {do it once for each chamber}
Begin
Side1[Ib]:=Distance[Ib];{one side of triangle already done}
Side2[Ib]:=SQRT(Sqr(XcBuf[1,Ib]−XcBuf[3,Ib])+Sqr (YcBuf[1,Ib]−YcBuf[3,Ib]));
Side3[Ib]:=SQRT(Sqr(XcBuf[1,Ib]−XcBuf[2,Ib])+Sqr (YcBuf[1,Ib]−YcBuf[2,Ib]));
End;
For Ib:=1 to 4 Do
SA[Ib]:=(Side1[Ib]+Side2[Ib]+Side3[Ib])/2.0;
For Ib:=1 to 4 Do
Begin
If ((SA[Ib]−Side1[Ib]>0.0) and (SA[Ib]−Side2[Ib]>0.0) and (SA[Ib]–Side3[Ib]>0.0)) Then
Begin
  Area[Ib]:=Sqrt(SA[Ib]*(SA[Ib]–Side1[Ib])*(SA[Ib]–Side2[Ib])* (SA[Ib]–Side3[Ib]));
  GlobalArea[Ib]:=GlobalArea[Ib]+Area[Ib]; {cumulate the areas across the session}
End;
End;

For calculation of the angle and direction of rotation, trigonometry and vector algebra are used. The distance formula is used to define a triangle with one of its vertices at the origin of the coordinate system (i.e., the geometric center of the upper surface of the force plate). Sample Calculation No. 5 shows a numerical example. This calculation provides the data upon which the estimate of rotation to the left or right is based. In other words this is the basis for the force plate serving as a rotometer.

The Pascal code for accomplishing this calculations is shown in the following Pascal Procedure.

Procedure CalcAngAndDir(x1,x2,x3,y1,y2,y3: Real;Box: Integer);
{for angles of rotation with respect to the origin for x1 use 0.0,
and for y1 use 0.0.x2,x3,y2,y3 are two successive time coordinates}
Var
a,b,c:Real;
Begin
a:=sqrt(sqr(x2–x1 )+sqr(y2–y1));
b:=sqrt(sqr(x3–x2)+sqr(y3–y2));
c:=sqrt(sqr(x3–x1)+sqr(y3–y1));
DirOfRot[Box]:=(x2–x1)*(y3–y2)–(y2–y1)*(x3–x2);
If (DirOfRot[Box]<0) then {these 2 If's exclude DirOfRot[Box]=0.0}
  Begin
  DirOfRot[Box]:=–1.0;
  NumRight[Box]:=NumRight[Box]+1;
  End;
If (DirOfRot[Box]>0) then
  Begin
  DirOfRot[Box]:=1.0;
  NumLeft[Box]:=NumLeft[Box]+1;
  End;
If (2*a*c) <>0.0 then CosOfRot[Box]:=(sqr(a)+sqr(c)–sqr(b))/(2*a*c);
If (CosOfRot[Box]<0.0) and (CosOfRot[Box]>–1.0) then
  Begin
  If (1–sqr(CosOfRot[Box]))>0.0 then
    TanOfRot[Box]:=(sqrt(1.0–sqr(CosOfRot[Box])))/CosOfRot[Box];
  AngOfRotR[Box]:=ArcTan(TanOfRot[Box]);
  AngOfRotD[Box]:=(–1.0)*((360.0/(2*Pi))*AngOfRotR[Box]);
    {change radians to degrees, because degrees better understood by more people}
  AngPlusDir[Box]:=AngOfRotD[Box]*DirOfRot[Box];
  End;
If (CosOfRot[Box]>0.0) and (CosOfRot[Box]<1.0) then
  Begin
  TanOfRot[Box]:=(sqrt(1.0–sqr(CosOfRot[Box])))/CosOfRot[Box];
  AngOfRotR[Box]:=ArcTan(TanOfRot[Box]);
  AngOfRotD[Box]:=((360.0/(2*Pi))*AngOfRotR[Box]);
  AngPlusDir[Box]:=AngOfRotD[Box]*DirOfRot[Box];
End;
If CosOfRot[Box]=–0.0 then AngPlusDir[Box]:= 90.0*DirOfRot[Box];
If CosOfRot[Box]=0.0 then AngPlusDir[Box]:= 90.0*DirOfRot[Box];
If CosOfRot[Box]=1.0 then AngPlusDir[Box]:= 0.0*DirOfRot[Box];
If CosOfRot[Box]=–1.0 then AngPlusDir[Box]:= 0.0*DirOfRot[Box];
If (AngPlusDir[Box]<0) Then
  RMeanAngle[Box]:=RMeanAngle [Box]+AngPlusDir[Box]
Else
  LeftmeanAngle[Box]:=LeftMeanAngle[Box]+AngPlusDir[Box];
End;

The angle-and-direction algorithm can also be used to calculate deviation from the current heading, yielding both an angle and a direction. This can be useful in an analysis of turning bias not referenced to the center of the chamber. For example, during stereotypies induced by dopamine agonists, a rat will stay in a circumscribed region of the chamber for minutes at a time, yet it may be turning within this space. The heading calculation when cumulated across time can provide an estimate of turning bias even though the animal does not make many (or any) circuits around the perimeter of the chamber. The current heading is calculated by replacing the origin (0,0) coordinates with the coordinates for the first of three successive points in time.

After the calculations of step 128, the program proceeds to step 130 where a five minute point determination is made. If the answer is "NO", the program proceeds back to the loop of steps 110–114 to step 104. When the step 130 is again reached and the answer is "YES", the program advances to step 132 where another distance, area, angle and direction calculation is made. At the conclusion of this calculation, the program again reverts to the loop of steps 110–114 and 104. At some point, of course, the step 114 query results in a "YES", and the program advances through steps 134–142 where calculations are made to reduce selected data, the data is printed and transferred to permanent memory, the RAM is cleared and the 4PLATES.PAS program is terminated.

That is, after the above-described real-time loops of the program have finished, calculations are completed for some variables and the results are printed in a readable format so that summaries of the behavior of the animals in each of the four chambers can be appreciated. This hard copy on paper is also produced as a backup procedure to ensure some data will be retained in the event media failure or investigator error results in the loss of the raw data that are stored on disk.

The Pascal code to accomplish the calculations and the formatted printing is as follows:
Procedure CalculateResults;
Begin
Writeln(Lst,FileName);
Writeln(Lst,'Box 1 ','Box 2 ','Box 3 ','Box 4 ');
Writeln(Lst,'Distance Traveled: ',
GlobalDistance[1]:10:0,GlobalDistance[2]:10:0, GlobalDistance[3]:10:0,
GlobalDistance[4]:10:0);
Writeln(Lst,'Area Measure: ',
GlobalArea[1]:10:0,GlobalArea[2]:10:0, GlobalArea[3]:10:0,
GlobalArea[4]:10:0);
For Ie:=1 to 4 Do
  Begin
  NForFz[Ie]:=SessionTime;

```
FSumForMean[Ie]:=FSumForMean[Ie]/NForFz[Ie];
End; {Fz means are now in FSumForMean}
For Ie:=1 to 4 Do
   FSumSqr[Ie]:=(FSumSqr[Ie]/NForFz[Ie])-(Sqr
      (FSumForMean[Ie]));
{Fz variances for session are in FSumSqr}
Writeln(Lst,'Mean Fz for session',
FSumForMean[1]:10:0,FSumForMean[2]:10:0,
   FSumForMean[3]:10:0,
FSumForMean[4]:10:0);
Writeln(Lst,'Variance for Fz :',
FSumSqr[1]:10:0,FSumSqr[2]:10:0,FSumSqr[3]:10:0,
FSumSqr[4]:10:0);
For Ie:=1 to 4 Do NetRots[Ie]:=(RMeanAngle[Ie]+
   LeftMeanAngle[Ie])/360.0;
Writeln(Lst,'Net Rots (-is to R)',
NetRots[1]:10:2,NetRots[2]:10:2,NetRots[3]:10:2,NetRots
   [4]:10:2);
{Calculate proportion of time spent in each Section}
For Ie:=1 to 4 Do TSSum[Ie]:=0.0;
For Ie:=1 to 4 Do
For Id:=1 to 64 Do TSSum[Ie]:=TSSum[Ie]+TS[1,Id,Ie];
For Ie:=1 to 4 Do
For Id:=1 to 64 Do TS[2,Id,Ie]:=TS[1,Id,Ie]/TsSum[Ie];
Writeln(Lst,'Prop time spent:');
For Ie:=1 to 4 Do
   Begin
   Writeln(Lst,'Box',Ie,' ');
   For Id:=1 to 8 Do
   Writeln(Lst,TS[2,Id,Ie]:7:3,TS[2,Id+8,Ie]:7:3,TS[2,Id+
      16,Ie]:7:3,
   TS[2,Id+32,Ie]:7:3,TS[2,Id+40,Ie]:7:3,TS
      [2,Id+48,Ie]:7:3,
   End;
For Ie:=1 to 4 Do {calculate distance by 5 min intervals}
   Begin
   Dby5[6,Ie]:=Dby5[6,Ie]-Dby5[5,Ie];
   Dby5[5,Ie]:=Dby5[5,Ie]-Dby5[4,Ie];
   Dby5[4,Ie]:=Dby5[4,Ie]-Dby5[3,Ie];
   Dby5[3,Ie]:=Dby5[3,Ie]-Dby5[2,Ie];
   Dby5[2,Ie]:=Dby5[2,Ie]-Dby5[1,Ie];
   End;
Writeln(Lst,'Distance by 5-min intervals within the
   session:');
Writeln(Lst);
Writeln(Lst,'1 2 3 4 5 6');
For Ie:=1 to 4 Do
   Begin
   Writeln(Lst,'Box',Ie,' ');
   Writeln(Lst,Dby5[1,Ie]:10:0,Dby5[2,Ie]:10:0,Dby5
      [3,Ie]:10:0,
      Dby5[4,Ie]:10:0,Dby5[5,Ie]:10:0,Dby5[6,Ie]:10:0);
   End;
Writeln(Lst,Char(12));{form feed}
End; {procedure}
```

After the 4PLATES.PAS program is completed, the OFFLINEP.PAS data reduction program (FIGS. 18A–18C) is operated to allow for the selection of key parameters which are chosen depending on the nature of the data and the scientific questions being addressed with the particular force plate actometer tests.

These parameters are: 1) the amount of moving average smooth applied to the raw data before the distance traveled and number of rotations are calculated; 2) the size of the circle that defines a bout of low mobility, where low mobility is of special interest in studies of stimulant induced stereotypies which are characterized by intense activity in "one place", i.e., the circle parameter defines quantitatively the size of the "one place"; 3) the interval of time that defines a bout of low mobility; 4) the number of separate square sectors that the force plate is divided into for purposes of performing a spatial analysis, i.e., how behavior is distributed across the surface of the force plate; 5) the number of successive time frames within a session as a means of analyzing behavior changes across time which is valuable in studying drug kinetics with behavioral end points; and 6) duration of the recording session.

Figure 18A:
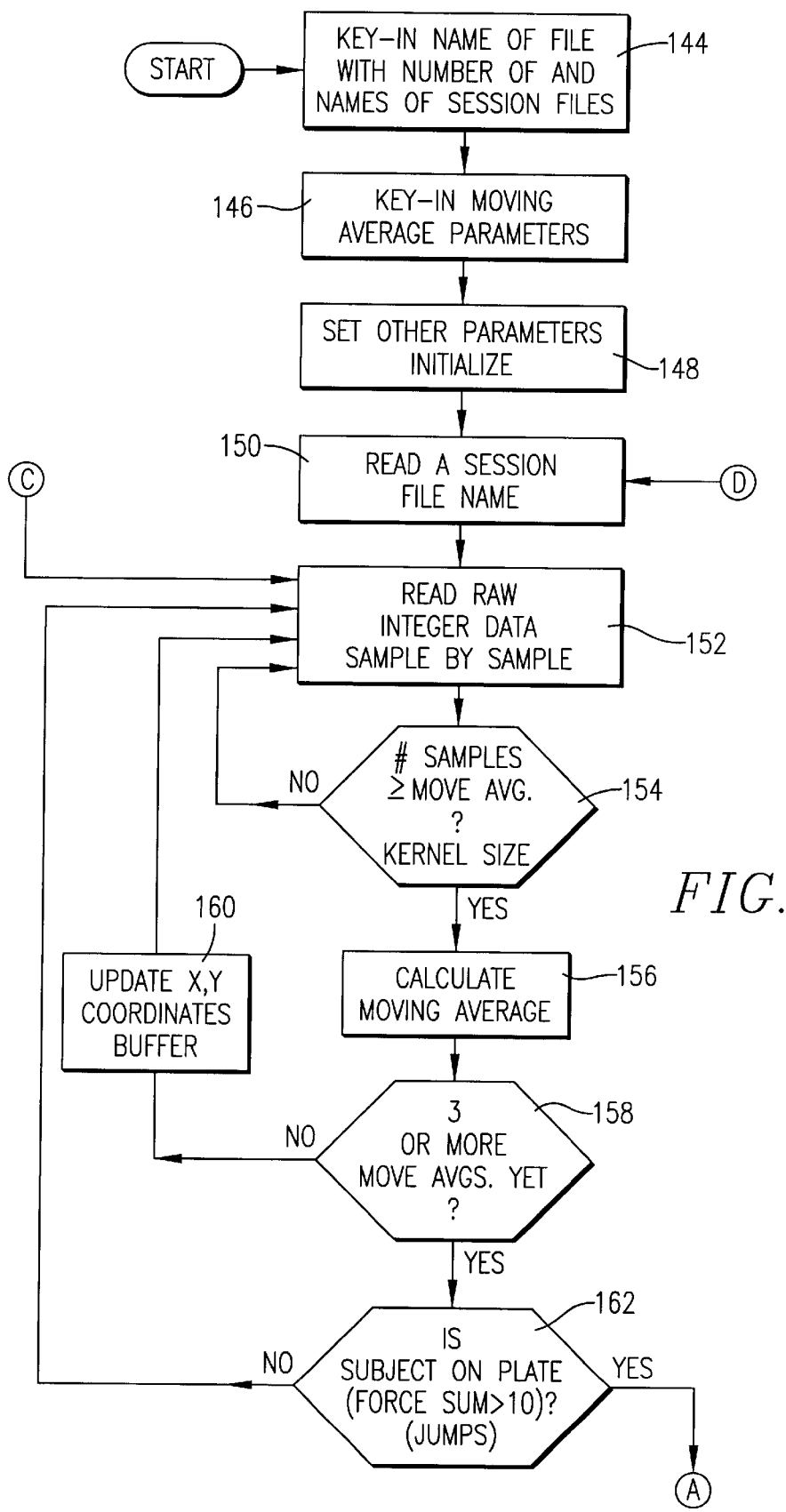
FIG. 18A is a portion of a flow diagram of one of the preferred software programs used in the invention, OFFLINEP.PAS.

Although the number of permutations and combinations of these parameters provides for a vary large domain of possible analyses, the scientific literature has served as a guide for narrowing the choice of parameters to a relatively few as embodied in the current working version of the program. For analyzing data on the low mobility and rhythmic movements induced by amphetamine sulfate the parameters were as follows:

1. moving average kernel=5
2. radius of circle defining low mobility=15 mm
3. required duration of 1 bout of low mobility=10.24 s
4. number of square sectors=64, each sector is a 35 mm square
5. number of separate within session time frames=45, at 40.96 s each
6. duration of recording session=nominally 30 min, in exact terms 45×40.96 s=1843.2 s (These parameters are established in steps 146 and 148 of FIG. 18A.)

The program OFFLINEP.PAS creates output into text files so that the data can be read and analyzed by commercially available software (such as AutoSignal, Systat, by SPSS Inc, or by spread sheet programs such as Microsoft's Excel). The names of the output files are currently fixed in the program so as to reduce human error and to provide a convenient naming scheme for describing the output. In addition, the filing scheme was designed to avoid the necessity of naming every file uniquely. Instead the unique identity of files is preserved by the subdirectory (folder) names where separate session data are individually stored. This is accomplished in step 144 (FIG. 18A).

The files written to disk are: ByFrame.txt, By5min.txt, Propt.txt, ??????T1.txt, ??????T2.txt ,??????T3.txt, ??????T4.txt (The question mark characters session name which is a parameter that varies with the actual data input).

The ByFrame.txt file contains the reduced data thought most likely to be of use to scientists studying the effect of drugs in mice or rats. This file contains 45 rows and 27 columns, which give data for 1 session of 4 animals with one animal in each of the 4 chambers used in the data recording. A separate ByFrame file is written for each session. These data are later assembled together in other packages such as Systat for further analysis. The variables contained in this file are defined in the following table.

The names of the variables in ByFrame.txt and the corresponding name in the Pascal program OFFLINEP.PAS and suggested names for importation by Systat. At the end of the table is sample code in Systat command language for reading one ByFrame file.

| Pascal Var | Systat Var | Description of measured value from the force plate |
|---|---|---|
| SmoothKernel | movavg | the moving average value used to calculate the smooth |
| Isess | sess | the session number giving the order of processing, for trouble shooting |
| FrameNo | frame | the frame number in a session, time within a session by 40.96 s intervals |
| FocAct[1] | sp1 | spatial statistic for chamber 1 (deviation from uniform distribution) |
| FocAct[2] | sp2 | spatial statistic for chamber 2 |
| FocAct[3] | sp3 | spatial statistic for chamber 3 |
| FocAct[4] | sp4 | spatial statistic for chamber 4 |
| FrameDist[1] | dpf1 | distance traveled per 40.96-s time frame chamber 1 |
| FrameDist[2] | dpf2 | distance traveled per frame chamber 2 |
| FrameDist[3] | dpf3 | distance traveled per frame chamber 3 |
| FrameDist[4] | dpf4 | distance traveled per frame chamber 4 |
| Bouts[1] | lm1 | number of low mobility bouts per frame, chamber 1 |
| Bouts[1] | lm2 | number of low mobility bouts per frame, chamber 2 |
| Bouts[1] | lm3 | number of low mobility bouts per frame, chamber 3 |
| Bouts[1] | lm4 | number of low mobility bouts per frame, chamber 4 |
| TBDist[1] | dpb1 | distance traveled per bout per frame, chamber 1 |
| TBDist[2] | dpb2 | distance traveled per bout per frame, chamber 2 |
| TBDist[3] | dpb3 | distance traveled per bout per frame, chamber 3 |
| TBDist[4] | dpb4 | distance traveled per bout per frame, chamber 4 |
| AvgDistPerBout[1] | adb1 | average distance per bout per frame, chamber 1 (stereotypy score) |
| AvgDistPerBout[2] | adb2 | average distance per bout per frame, chamber 2 |
| AvgDistPerBout[3] | adb3 | average distance per bout per frame, chamber 3 |
| AvgDistPerBout[4] | adb4 | average distance per bout per frame, chamber 4 |
| NetRots[1] | ro1 | Net rotations cumulated across frames, chamber 1 (- is cw) |
| NetRots[2] | ro2 | Net rotations cumulated across frames, chamber 2 (- is cw) |
| NetRots[3] | ro3 | Net rotations cumulated across frames, chamber 3 (- is cw) |
| NetRots[4] | ro4 | Net rotations cumulated across frames, chamber 4 (- is cw) |

Sample Systat Command language code:
new
get c:\032201\byframe.txt
input movavg,sess,frame,sp1,sp2,sp3,sp4,dpf1,dpf2,dpf3,dpf4,lm1,lm2,lm3,
lm4,dpb1,dpb2,dpb3,dpb4,adb1,adb2,adb3,adb4,ro1,ro2,ro3,ro4
save c:\workarea\hd3s1.syd
run The file By5min.txt contains the distance traveled variable recorded in 5-min intervals. This is redundant with data in ByFrame.txt, but may serve the needs of investigators who only want to study total movement in time blocks appropriate for addressing questions related to habituation, hypoactivity, or hyperactivity.

The file Propt.txt provides data on the percent of time the animal spent in each of the 64 sectors of the force plate. This information is on a time frame basis, i.e., calculated separately for each 40.96-s time frame within the session. The percent time is of interest to scientists studying how amphetamine and related drugs influence an animal's use of space. This calculation may also be quite revealing in contexts where the force plate actometer is used as the floor of an operant chamber. In this latter case the percent time spent in the vicinity of the reward well or the operant lever can be measured.

Time series data files (e.g., ??????T1.txt) associated with each bout of low mobility are written for each chamber so that the frequency characteristics of these movement can be quantitated. This is a major novel feature of the force-plate-computer-program ensemble. The size of each file depends on the number of bouts of low mobility exhibited by each subject. However, all files have the same general format with the first column of data containing the successive time values within a bout (i.e., 512 time point with 0.02-s spacing) and the additional columns containing the values of the Fz forces across time. The Fz force is the resultant vertical force obtained by summing the forces on each of the 4 transducers for each time point sampled. The data format is convenient for Excel and subsequently for AutoSignal commercial packages so that Fourier analysis or other frequency and/or power analyses (such as wavelet analysis) can be performed.

Initialization of the arrays and variables needed for the calculations in OFFLINEP.PAS is given by the following Pascal code:

For Ix:=1 to 4 Do {initialize summing arrays for all 4 chambers' data}
  Begin
  Xc[Ix,1]:=0.0; Xc[Ix,2]:=0.0;pXc[Ix]:=0.0;
  Yc[Ix,1]:=0.0; Yc[Ix,2]:=0.0;pYc[Ix]:=0.0;
  StXc[Ix]:=0.0; StYc[Ix]:=0.0;
  {StXc[Ix] and StYc[Ix] set the initial starting point for defining the first low mobility bout. This is arbitrary. Any valid coordinates would be okay.}
  Tally[Ix]:=0; Bouts[Ix]:=0; NumBTS[Ix]:=1;
  Fsum[Ix]:=0.0;
  GlobalDistance[Ix]:=0.0;
  GlobalArea[Ix]:=0.0;
  Distance [Ix]:=0.0;
  FrameDist[Ix]:=0.0;
  BoutDist[Ix]:=0.0;
  TBDist[Ix]:=0.0;
  Area[Ix]:=0.0;
  For Ixx:=1 to 6 Do Dby5[Ixx,Ix]:=0.0;
  FSumSqr[Ix]:=0.0;
  FSumForMean[Ix]:=0.0;
  TMean[Ix]:=0.0;
  TSumSqr[Ix]:=0.0;
  NumLeft[Ix]:=0.0; NumRight[Ix]:=0.0;
  LeftMeanAngle[Ix]:=0.0; RMeanAngle[Ix]:=0.0;
  FrameNo:=0;
  End;

In step 150, the programs reads a session file name and commences the desired calculations. The session file name is in a text file prepared in advance and stored on disk. First, the raw integer data is read sample by sample in step 152 and the program advances to step 154 where the program determines whether the number of samples is greater than or equal to the moving average (kernel size). If the answer is "NO", the program loops back to step 152 until a "YES" is obtained. At this point, a moving average is calculated in step 156 and, in step 158, the program determines whether three or more moving averages have been obtained. If the answer is "NO", the program updates the X, Y coordinates buffer (step 160) and returns to step 152. This is continued until a "YES" answer is obtained. In the next step 162, the program determines whether the subject is on the plate by determining whether the force sum is greater than 10. This is to account for jumping of the subject. If the answer is "NO", the program again loops back to step 152. If the answer is "YES", the X, Y coordinates buffer is updated in step 164 and calculations are performed in step 166.

Distance, area, and rotation calculations are performed in step 166 just as they were in the data acquisition program 4PLATES.PAS, as described previously. In addition, however, OFFLINEP.PAS calculates a spatial statistic that gives a measure of how concentrated in space the animal's behavior was in a given time frame. The basic idea is to calculate a Chi Square-like statistic that reflects the degree to which the distance traveled in each of the 64 square sectors of the force plate deviates from a uniform distribution. In this case a uniform distribution is defined as all 64 squares equal to each other in distance traveled. For an animal, a uniform distribution is virtually impossible; however, rats and mice typically visit more different sectors of the chamber floor during their initial minutes in the chamber. During the exploratory periods the distribution of movements is closer to uniform than later in the session when the animal will increasingly tend to stay in "one place." This spatial statistic provides a way to measure spatial stereotypy such as repeatedly taking the same path around the chamber. Amphetamine induces such behavior in some strains of mice, and during the path stereotypies the spatial statistic tends to display low variability from time frame to time frame. Sample Calculation No. 6 gives two examples of the application of this algorithm, which is expressed in Pascal code as follows:

For Id:=1 to 64 Do TS[2,Id,Ie]:=TS[1,Id,Ie]/TsSum[Ie];
{sum the distances across 64 sectors for this time frame}
{discrepancy calc here, for all 4 chambers}
For Ie:=1 to 4 Do
For Id:=1 to 64 Do
TS[5,Id,Ie]:=Sqr((Ts[2,Id,Ie]*100)−1.5625);{squared deviations from uniform distribution}
For Ie:=1 to 4 Do FocAct[Ie]:=0.0;
For Ie:=1 to 4 Do {get sum of squares}
For Id:=1 to 64 Do
FocAct[Ie]:=FocAct[Ie]+TS [5,Id,Ie];
For Ie:=1 to 4 Do FocAct[Ie]:=Sqrt(FocAct[Ie]);
{Square root of the sum of squares gives the spatial statistic. 0 means no deviation from uniform, and 99.216 is maximally deviant from uniform based on 64 sectors.}

The program then proceeds to step 168 where it determines whether the current point is less than 15 mm from the bout start point. If the answer is "NO", the bout registers are reset and a new bout starting point is chosen (step 170). Next, the program proceeds to step 172 where it determines whether an exact 5-minute point has been achieved. If the answer in 168 is "YES", the program moves to step 169 where unfiltered force data and increment bout time distance are placed in the time series array. This is followed by step 169a where the program determines whether the bout time is greater than the bout criterion time. If the answer is "NO", the program proceeds to step 172. If the answer "YES", the programs moves to step 169b where increment bout count distance and time series are indexed for sequential storage. Then the program advances to step 172.

Figure 18B:
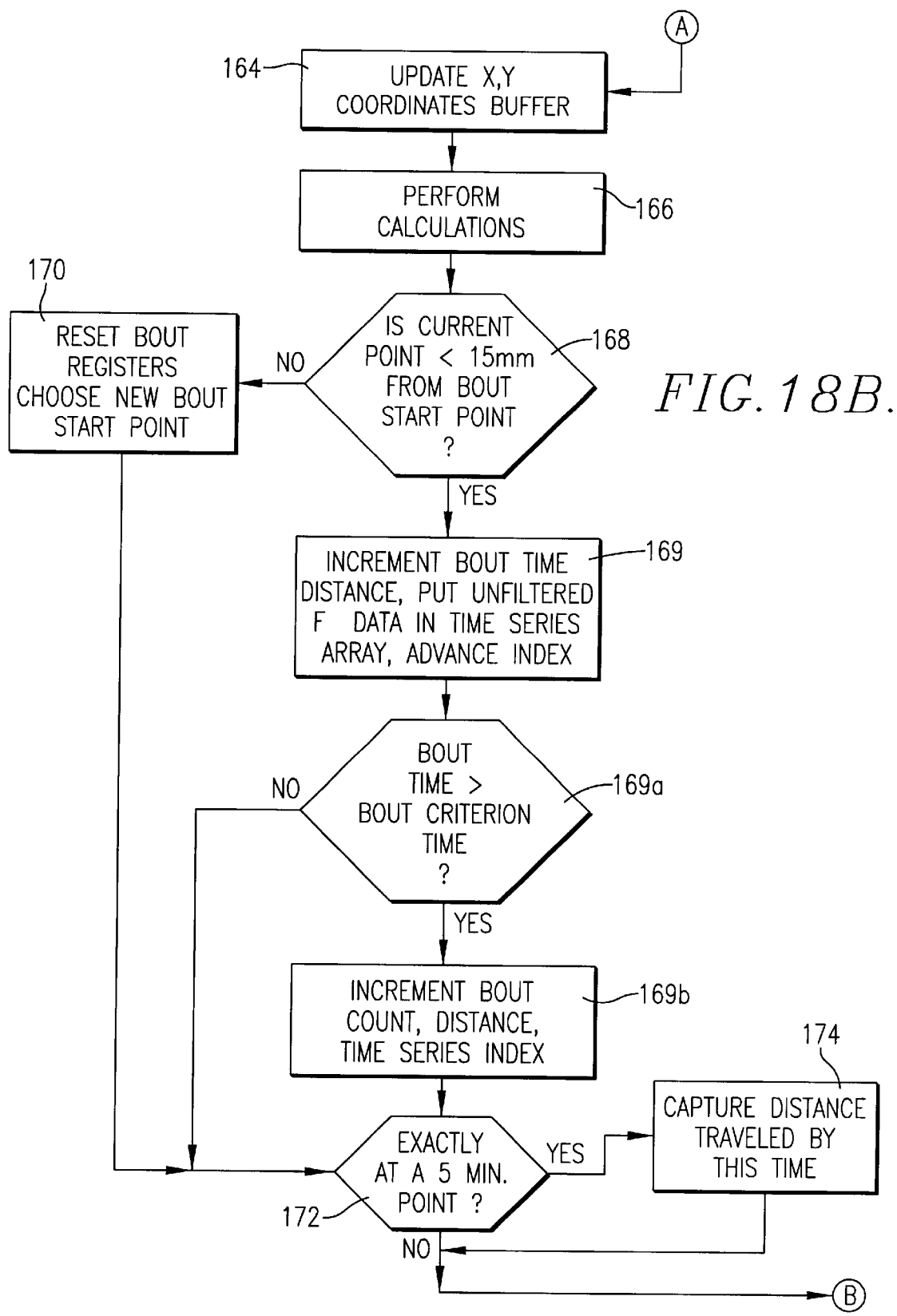
FIG. 18B is a continuation of the flow diagram of FIG. 18A.
Figure 18C:
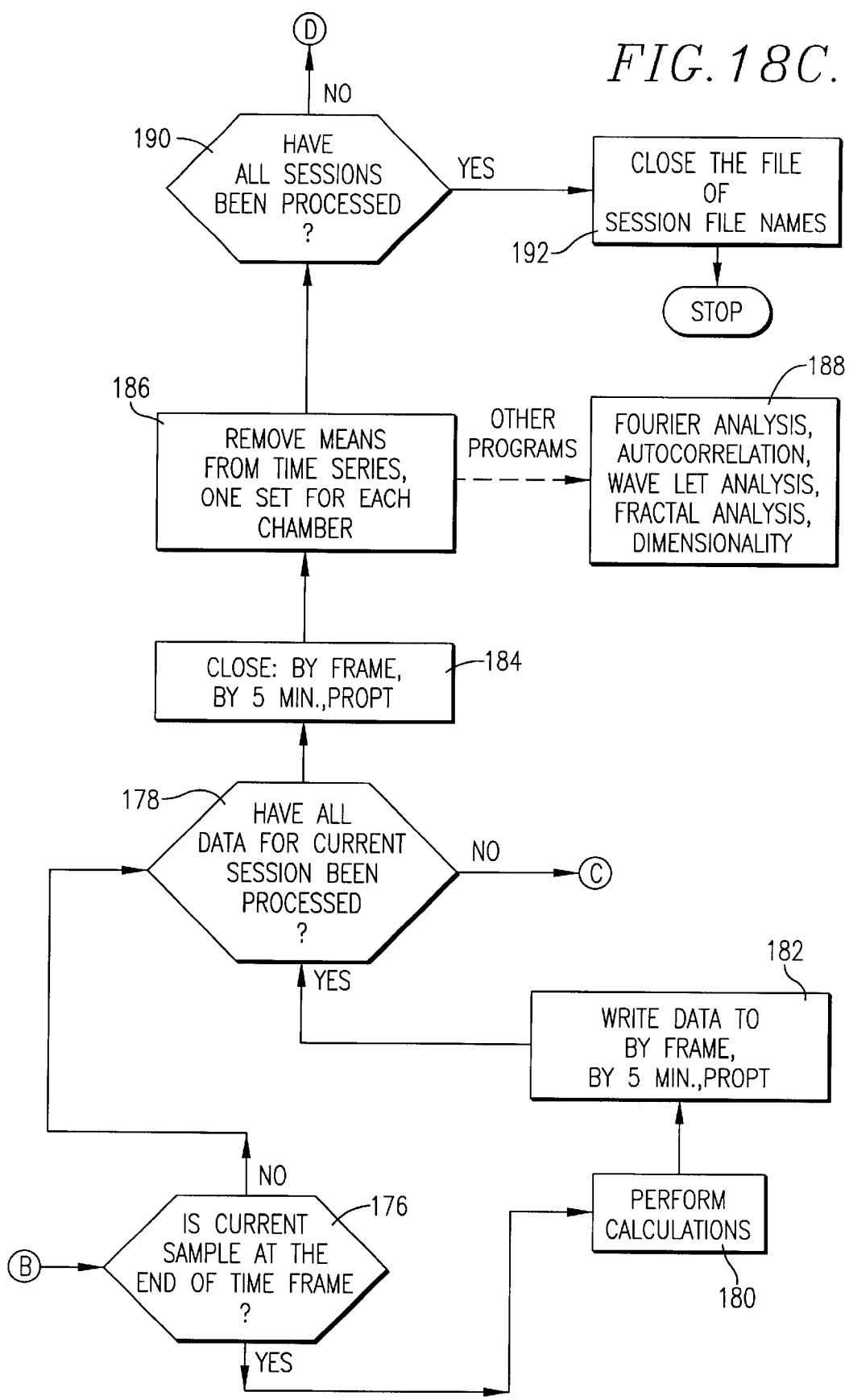
FIG. 18C is a further continuation of the flow diagram of FIG. 18B.

If the answer to the query of step 172 is "YES", the program captures the distance traveled by this time in step 174, and the program proceeds to step 176 (FIG. 18C). Likewise, if the query in step 172 results in a "NO" answer, the program goes to step 176. In step 176, the program determines whether the current sample is at the end of the time frame. If the answer is "NO", the program proceeds to step 178. If the answer at step 176 is "YES", the program proceeds to step 180 where additional calculations are performed. In step 182, the data is written by frame and the program moves to step 178.

The calculations performed in step 180 are at the end of each time frame mainly and involve data manipulations to ensure that the data sent to the file correspond to the specific time frame in question. A novel calculation involves the computation of the stereotypy score for a particular frame. At higher, but not convulsive doses, amphetamine (and related stimulants such as cocaine) induce in rats a state characterized by low amounts of locomotion and large amounts of head movement and oral movements. This syndrome is termed "Stereotypies." These stereotypies are generally measured by experimenter visual observation and rating scales. The stereotypy score calculated by OFFLINEP.PAS quantitatively defines bouts of low mobility in spatial coordinates (confining movements of the center of force to a 3 cm diameter circle) and a time criterion of at least 10.24 s in this circumscribed space. Importantly, the 3 cm diameter circle is not located by any fixed attribute of the apparatus, but is rather defined by the animal's behavior. The computer program finds these bouts of low mobility. Even though the animal is not locomoting under the influence of amphetamine, it is exhibiting considerable movement which is sensed by the force plate as small translations of the center of force. These displacements are measured while the animal is meeting the quantitative criterion for low mobility in the locomotion sense of these words. The stereotypy score is the average amount of distance the center of force moves per bout of low mobility. In addition, this stereotypy score is provided as a function of session time (i.e., it is calculated for each of the 45 frames of a session). Thus, the development of the stereotypy "syndrome can be tracked in time with high resolution in each subject. The rhythmic nature of the stereotypies is calculated by performing Fourier analyses or alternatively wavelet analyses on the time series written to disk for each bout of low mobility.

In Pascal code, the stereotypy score is the distance accumulated during low mobility bouts during one frame (40.96 s) divided by the number of low mobility bouts detected in that frame.

For Ie:=1 to 4 Do
If Bouts[Ie]>0 then
AvgDistPerBout[Ie]:=TBDist[Ie]/Bouts[Ie]
else AvgDistPerBout[Ie]:=0.0;

At step 178, the program determines whether all data for the current session has been calculated. If the answer is "NO", the program loops back to step 152 until all data is processed. This causes the program to advance to step 184 which closes the files ByFrame.txt, By5Min.txt and Propt-.txt. Next, in step 186 the means are removed from the time series, one set for each chamber. At this point, if desired, other programs may be utilized to reformat the data for specialized analyses as well as for carrying out algorithms for detecting specific kinds of behavior, such as "wall rearing" (step 188).

In order to measure tremor using Fourier analysis, data must be prepared in the proper format for the Fourier analysis program. A utility program PREPFZ.PAS is used to extract the information from the raw integer files and to rearrange it for processing by Alligator Technologies Fourier Perspectives III. Data can be analyzed either in terms of the Fz force (sum of the 4 transducers) or as individual separate transducers. After Fourier processing, thousands of resulting power spectra need to be imported into a statistics package such as SYSTAT. The utility program for reading the individual power spectra and assembling then into files for each animal's recording session is FZMERG.PAS. SYSTAT command files are then used to manipulate these data both statistically and graphically.

Other utility programs are needed to obtain plots of the spatial trajectories of the animal's movements on the force plate during a session. MAKEDIST.PAS reads the raw data, calculates the x-y coordinates, and transforms these data into a form suitable for importation into SYSTAT or other graphics package. Then SYSTAT command language files are used to plot the data frame-by-frame.

The preferred force plate actometer of this invention provides data that, when appropriately filtered and processed, provides estimates of the number of wall rears that an animal makes. This is of importance in pharmacology and behavioral genetics studies because some drugs are known to suppress rearing, and genetic endowment influences mouse rearing behavior. It is possible to detect wall rearing because when the mouse rears on hind legs and presses its forepaws against the side of the enclosure a substantial proportion of its body weight is transferred to the wall which is suspended above the force plate. Thus, the wall rear produces a substantial downward deflection in the Fz force record, followed by recovery of Fz to the body weight when the mouse comes down from the rear. The wall rearing algorithm searches through a data set mouse-by-mouse looking for events that qualify as wall rears. Not only does the program count the rears, but it also measures their intensity (degree of off loading from hind feet to wall) duration, and the time between rears. The wall rearing algorithm works as follows: 1) the raw data are smoothed with a moving average kernel of 5; 2) a rear-begins-detection threshold is selected based on empirical experience; this defines the amount of downward deflection in Fz required to register the beginning of a rear; 3) an rear-completion threshold is also specified for determining when the rear has ended. Data from four chambers are concurrently expressed as the smoothed Fz values, and these are processed in a stream from the beginning of the session to the end of the session. The rears are quantified according to occurrence, intensity, duration of the rear, and time between the rears.

The program was validated by comparing the results from a human observer viewing video tapes taken from 30-min sessions of force plate recording for two mice: one BALB/c and one C57BL/6 mouse, two very genetically different mice. In terms of number of rears for the BALB/c mouse the video scored and computer scored wall rears were correlated +0.842 across 30 1-min blocks of the session. The correlation for the C57BL/6 mouse was +0.759 (probably lower because this mouse is black and is hard to see on the video tape with the viewing conditions available). When the algorithm was applied to 4 mice of each type the results showed that the BALB/c mice had a mean of 92.5 rears and the C57BL/6 mice had a mean of 70.8 rears, a difference that was statistically significant t(6)=2.861, p=0.029. Amphetamine treatment (2.5 mg/kg) robustly reduced the rears in both groups: BALB/c had a mean of 3.75 rears/session and C57BL/6 has a mean of 3.5 rears/session, both results were highly significant.

After step 186 and the optional step 188, the program proceeds to step 190 to determine whether all sessions have been processed. If the answer is "NO", the program loops back to step 150 until all sessions are processed and a "YES" is obtained. The program then closes the file of session file names (step 192) and stops the program.

EXAMPLES

The following examples set forth presently preferred techniques for utilizing the force actometer of the invention. It is to be understood, however, that these examples are provided by way of illustration and nothing therein should be taken as a limitation upon the overall scope of the invention.

Example 1

Instrument-scored Stereotypies Induced by D-amphetamine in Rats Purpose

Amphetamine and other drugs that increase the brain action of the neurotransmitter dopamine induce in rats a state of behavioral activation that at low doses produces increases in locomotor activity and at high doses leads to highly repetitive, rhythmic behaviors such as nose poking, sniffing, and licking, but no locomotion. These high-dose phenomena are collectively referred to as stereotypies. These behaviors related to increased dopamine function in the brain are of great interest to scientists because dopamine is known to be involved in a wide range of human disorders and diseases such as schizophrenia and other psychoses, attention deficit hyperactivity disorder, drug addiction, and obsessive compulsive disorder. Moreover, substantial evidence implicates dopamine in learning processes and in Parkinson's disease. Locomotor activity and stereotypies in rats are model responses for scientist to study the pharmacology and physiology of brain dopamine systems at the behavioral level of expression.

Method

The subjects were male Sprague-Dawley rats about 4 months old at the time of the treatments. Nine rats received amphetamine injections and 8 separate rats got physiological saline injections. These rats weighed about 350 g each and were obtained from Harlan Co., Indianapolis, Ind.

The apparatus was four concurrently operating force plate actometers as described previously.

Rats in the amphetamine group were injected (ip.) with d-amphetamine sulfate 3.0 mg/kg 15 min before being placed in the chambers for 30 min of recording. Amphetamine injections were administered on three separate occasions spaced 2 weeks apart for each amphetamine group rat. Data from the 3rd session, when stereotypies were expected to be intense, were used for the analyses. Rats in the saline group received ip injections of physiological saline before recording sessions on three separate days. Data from the 3rd day were used for comparison with the amphetamine group.

Data were analyzed with the computer program OFFLINEP.PAS (FIGS. 18A–18C) and with additional techniques available in Systat. The program OFFLINEP.PAS identified bouts of low mobility, defined as periods of no locomotion outside of a 30 mm diameter circle for 10.24 s. Corresponding records of the force variation during the same time frame were stored so that the rhythmic components of behavior could be quantified with Fourier analysis. The basic concept was to define stereotypy as the intensity and rhythm of behavior occurring in "one place" under the influence of a stereotypy-inducing dose of amphetamine and to compare these measures to animals "staying in one place" but not under the influence of a drug.

Results

FIGS. 1 and 2 show two plots; in both plots the thick line represents the mean for the amphetamine group and the thin line represents the group mean for the saline control group. The abscissas give the time within the recording session in 45 equal interval blocks. Brackets indicate +/−1 standard error of the mean. The top set of axes shows that the amphetamine and control groups displayed comparable amounts of low mobility bouts across the session. The low numbers of low mobility bouts at the beginning of the session reflect the habituation of the control rats to the chamber (i.e, locomotor activity early in the session). The amphetamine rats had few low mobility bouts early in the session probably for the same reason. Additionally, in the drugged rats the rising curve across time charts the tendency for the stereotypies to intensify as the brain level of the drug peaks. The stereotypy scores in the lower set of axes in FIG. 2 show that although both groups of rats exhibited about the same level of bouts of immobility across the session (4 is the maximum possible per frame), the amphetamine rats were very active when they were in "one place." Visual observations of the amphetamine rats upon their removal from the recording chamber indicated that all nine rats were engaged in classical nose poking, sniffing, and head-weaving stereotypies.

Figure 3:
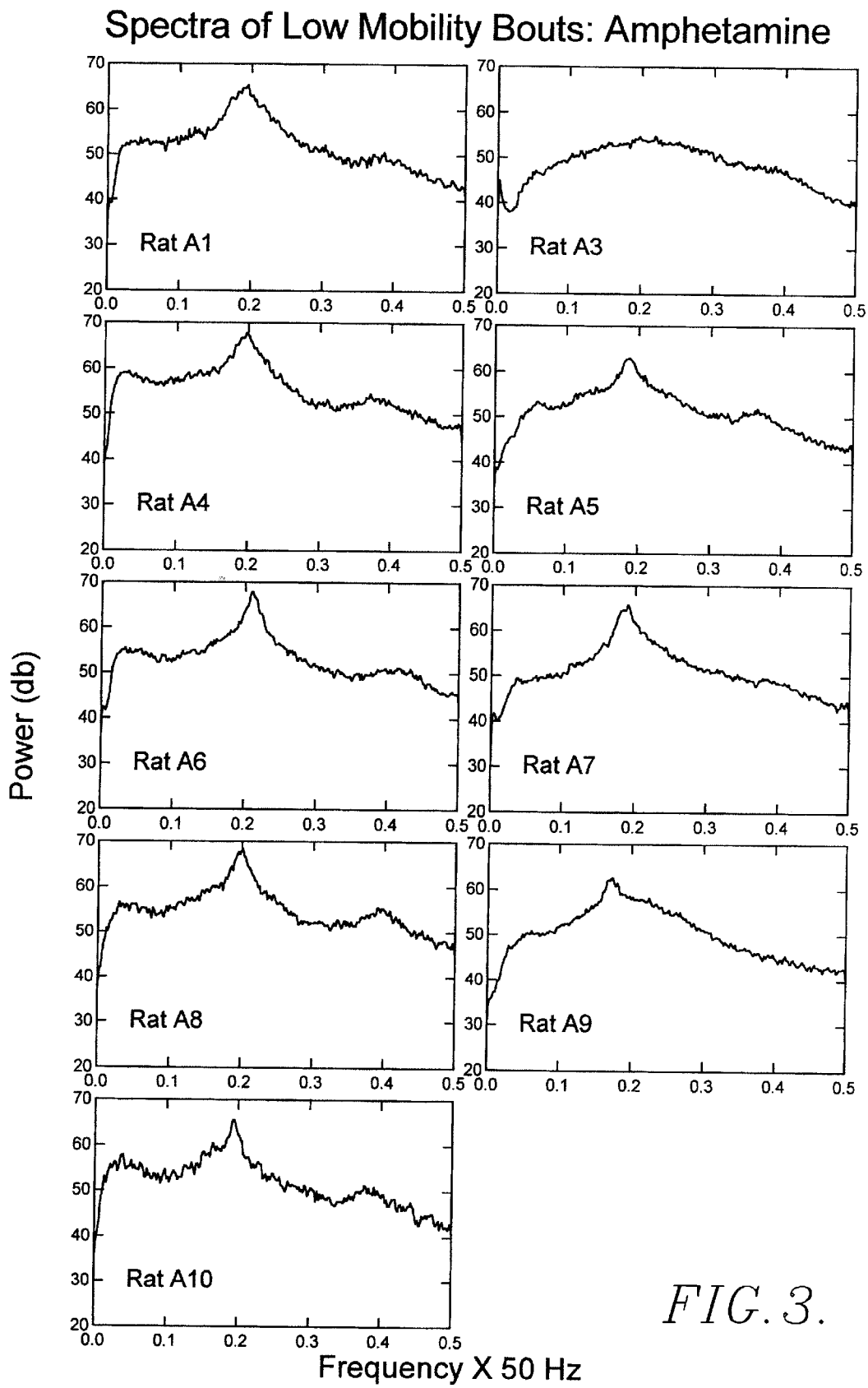
FIG. 3 is a series of nine power spectra for each bout of low mobility observed in the test of the amphetamine-treated rats, as described in Example 1.
Figure 4:
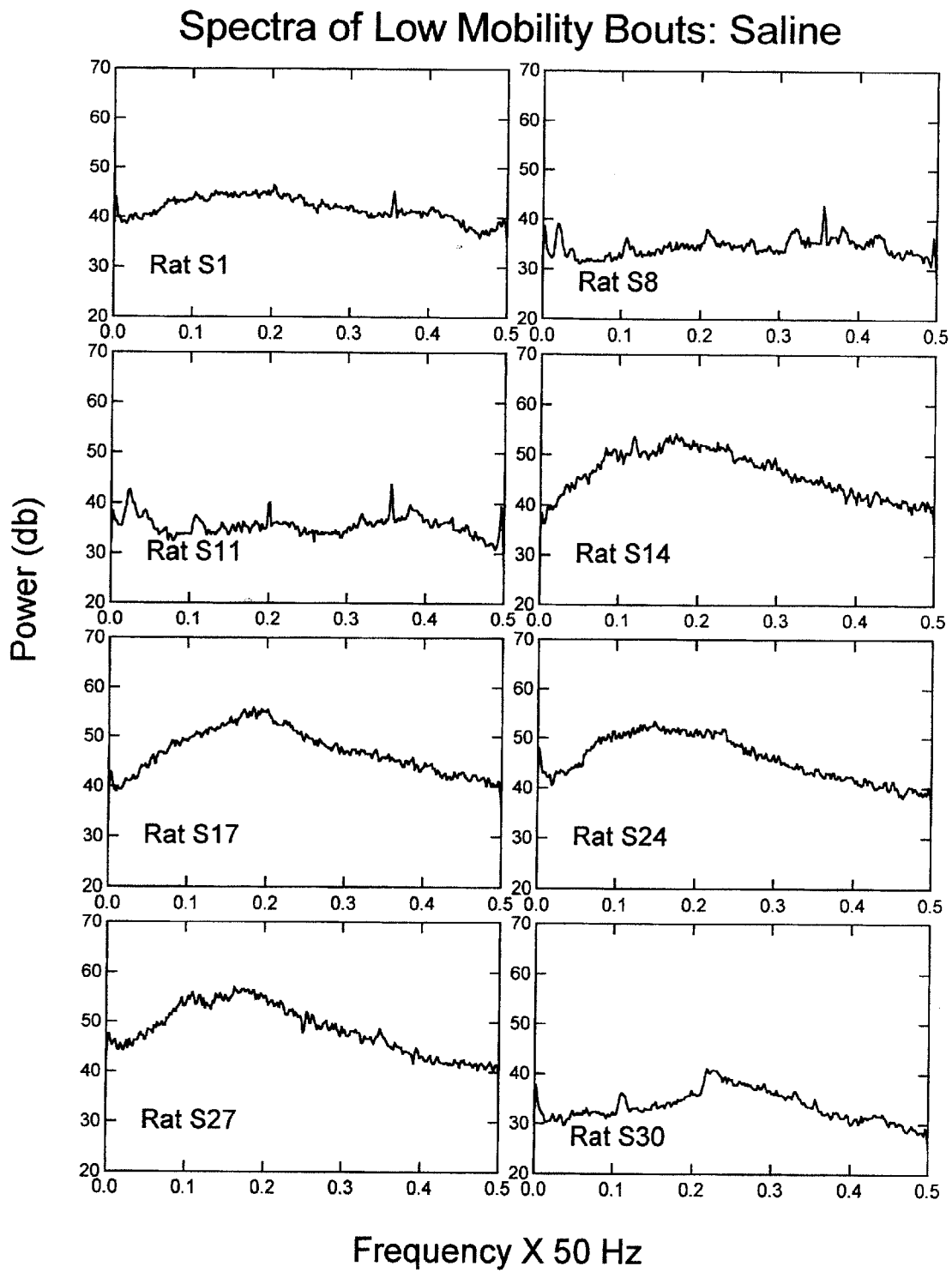
FIG. 4 is a series of eight power spectra for each bout of low mobility observed in the test of the control rats, as described in Example 1.

FIG. 3 exhibits the results of the Fourier analyses for the amphetamine rats. These data for each rat are the power spectra from the force records recorded during the low mobility bouts. A power spectrum was computed for each bout of low mobility and then these were averaged to obtain the functions shown in FIG. 3. Strong rhythmicity is apparent in the 8–11 Hz range (0.2 on the x-axis corresponds to 10 Hz), and there is a distinctive lack of low frequency power below about 0.5 Hz. The amphetamine data stand in distinctive contrast to the control group's data shown in FIG. 4; for the controls the power is 10–20 db less than for the amphetamine rats, and there is no 10-Hz peak. These are the first observations of this kind ever made, insofar as is presently known.

Conclusions

The force plate actometer and associated software can successfully "machine score" amphetamine-induced stereotypies.

In addition, by using the techniques hereof, it is now possible to discriminate between stereotypes produced by different agents, e.g., amphetamine, cocaine, apomorphine, SKF38393 and Quinpirole, to determine the extent to which dopamine blocking drugs alter the characteristics of the frequency components of stereotyped behaviors; the affect of brain manipulations (e.g., striatal lesions) upon components of movement that contribute to the distinctive power spectra seen for amphetamine treated rats. All of this information may have significant implication for the treatment of human diseases and conditions.

Example 2

Quantification of Harmaline-induced Tremor in Rats

Purpose

The drug harmaline is used to induce whole-body tremor in animals. The tremor induced is believed to be related to the olivocerebellar system in the brain, and harmaline tremor in animals is currently the most prominent laboratory animal model of essential tremor, a clinical condition in humans often involving tremor so severe that individuals cannot feed or hydrate themselves using conventional utensils (forks, cups, etc.).

Method

Thirty-two male Sprague Dawley rats from Harlan Co, Indianapolis, Ind., were studied.

The apparatus was the force plate actometer, described above, with no adjustments or modifications. If one were to use the instrument primarily for tremor studies, it would be possible to "tune" it for such purposes. For example, sessions of recording shorter than 30 min may be preferred and a sampling rate of 100 Hz or more may be desirable.

The rats were divided into 4 separate groups of 8 rats each. Separate groups received different doses of Harmaline hydrochloride as follows: 0.0 (saline), 4.0, 8.0, and 16.0 mg/kg, ip, 1–2 minutes before being placed in the recording chamber.

Data from the 30-min sessions were broken into 45 equal-length intervals of 40.96 s (or 2048 samples at a sampling rate of 50 Hz). These data were then subjected to Fourier analysis, and the power spectra for each rat and each 2048 segment of data were retained (32 rats×45 spectra/rat=1440 power spectra). Then, a tremor index was computed for each power spectrum. The tremor index was the difference between the average power in the 0.02–4.980 Hz frequency band and the 5.005–15.015 Hz frequency band of each power spectrum. This calculation emphasizes the peaking of the spectrum in the 5–15 Hz frequency band regardless of the absolute power level of the spectrum. A session average of the tremor index was obtained for each rat. Dose-effects statistical analyses were performed with one-way analysis of variance.

Results

Figure 5:
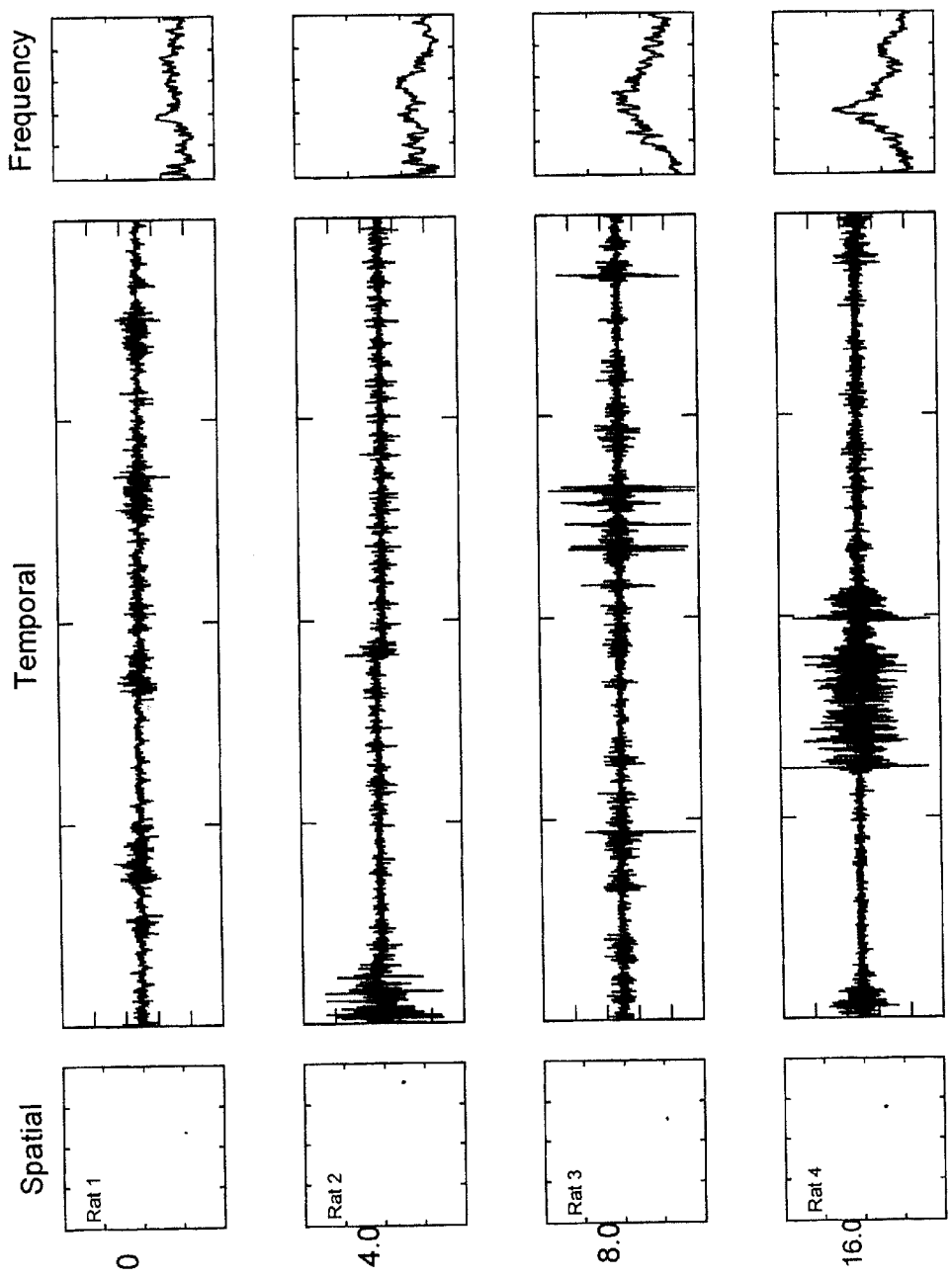
FIG. 5 is a series of four comparative graph sets derived from the test of Example 2.

Data from one rat in each of the four dose groups are shown in FIG. 5. These data are for one of the 45 time frames when the animals did not move from one spot as indicated by the dot in the spatial representations in the left column of axes in FIG. 5. The space enclosed by the axes represents the perimeter of the force plate (280×280 mm square). The corresponding time series of the Fz force (minus the mean) are shown in the middle column of axes; these tracings are for 40.96 s of recording. The Fz force is the sum of the forces from the four transducers at the corners of the force plate. In the right column of axes in FIG. 5 are the power spectra for the corresponding temporal plots. The peaking in the power spectra for the two higher doses of harmaline is pronounced; the ordinate of these plots cover 60 db.

Figure 6:
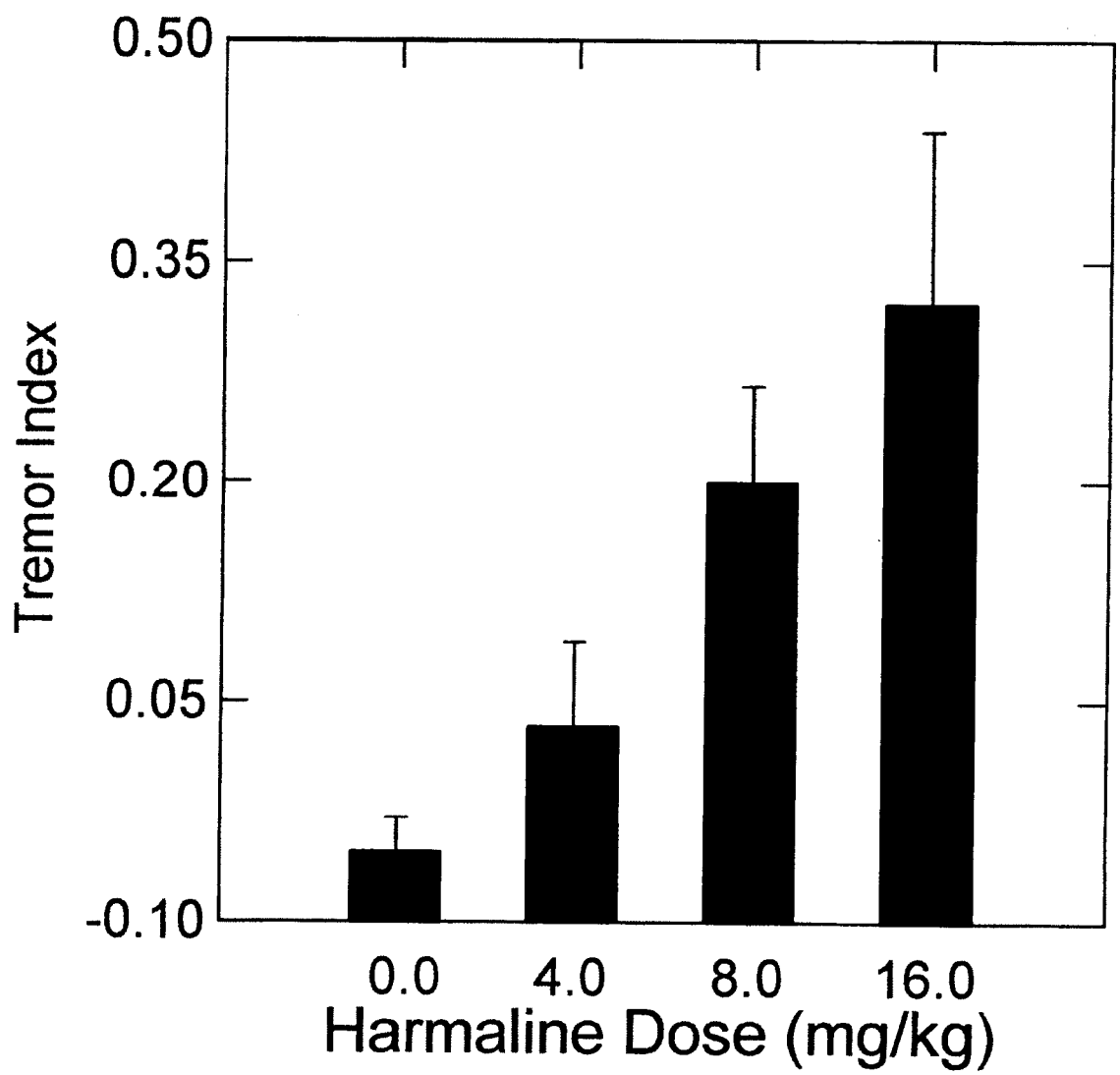
FIG. 6 is a graph of tremor index versus Harmaline-dose from the Example 2 tests, showing the effect of Harmaline dose on tremor behavior.

FIG. 6 illustrates the dose-effect data for the effect of harmaline on the tremor index. The drug effect is statistically significant, $F (3,28)=5.090$, $p=0.006$, and log linear as expected for dose-effect functions.

The force plate actometer provides a way for assessing the effects of the drug on locomotor activity in the same session that the tremor was recorded. This analysis showed that harmaline dose-relatedly suppressed locomotor activity, $F(3, 28)=6.514$, $p=0.002$, and the latency to the first bout of low mobility was also significantly shortened by the drug, $F(2, 28)=3.222$, $p=0.038$.

Conclusions

Without special modification the force plate actometer successfully measured harmaline tremor in a dose-related manner. In addition, the experiment quantified the tendency for harmaline to suppress locomotor activity. Tremor is a prominent symptom of heavy metal poisoning (lead, mercury, manganese), and other toxic substances such as organophosphate pesticides. Thus, the force plate actometer may be used as a tool in neurotoxicology studies in rodents.

Example 3

Rotational Behavior Induced by D-amphetamine in Rats Unilaterally Lesioned by Injection of 64-hydroxydopamine into the Substantia Nigra (Parkinsonism Model)

In the early 1970's the Swedish scientist Urban Ungerstedt showed that rats sustaining a neurotoxic lesion to the nigrostriatal pathway on one side of the brain will rotate to the side of the lesion (right side lesion results in rotations to the right) when challenged with amphetamine. The lesioned rat was placed in a 10" diameter bowl and observed for 30 or so min after the injection. It soon became apparent that the lesioned rat could be fitted with a harness and, by way of a tether, the harness could be attached to a rotary counter, thereby eliminating the need for a human observer to count the turns made by the rat. This unilateral lesion stimulant-induced rotation model has become the world's most popular laboratory model of Parkinson's disease. Drugs that are clinically useful in treating human Parkinson's disease are often effective in attenuating the rotations induced by amphetamine in these unilaterally lesioned rats.

Method

These rats met the same specifications as those used in Examples 1 and 2.

Figure 20:
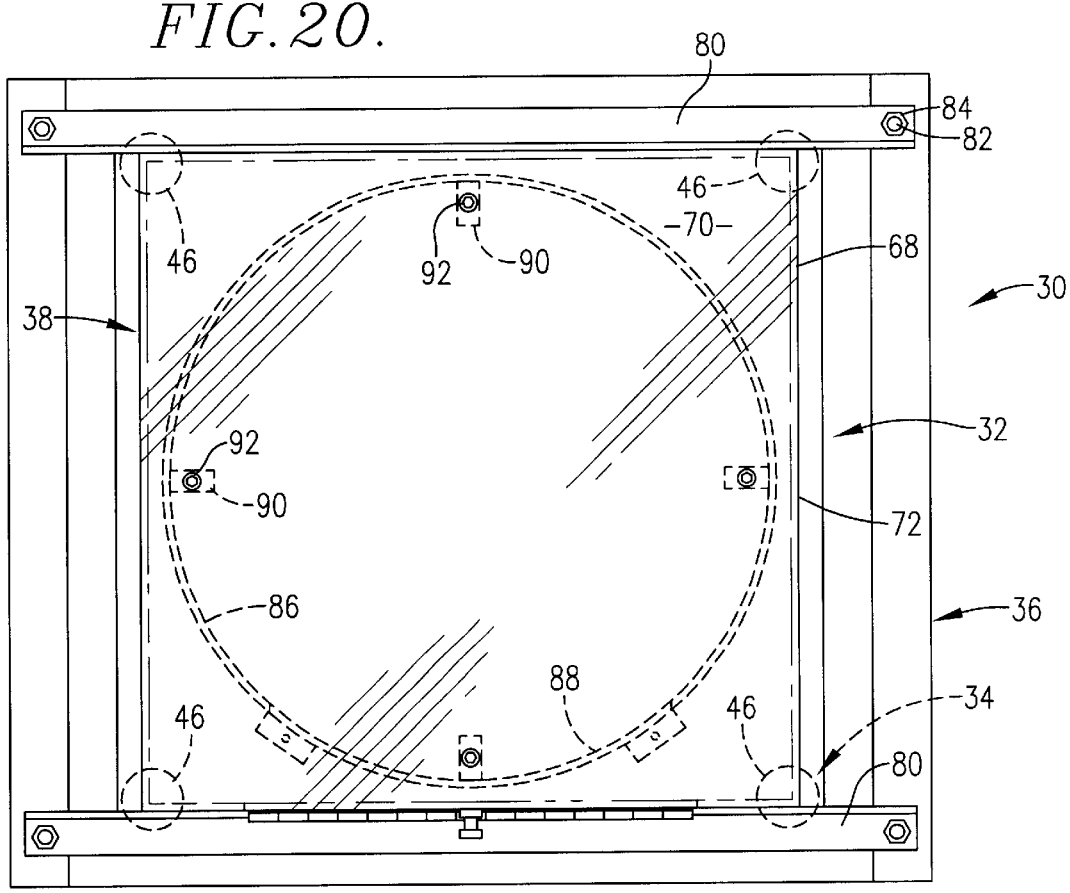
FIG. 20 is a plan view of the preferred force plate actometer apparatus, with the corner-mounted force transducers depicted in phantom.

The apparatus was the force plate actometer with the cylindrical insert installed as depicted in FIG. 20. This insert presents the rat with a circular arena in which it can move. Note that neither harness nor tether was used. The rotations were calculated by the computer from the position coordinates derived from the force plate.

Rats were lesioned with the neurotoxin 6-hydroxydopamine. Surgery was performed under ketamine plus xylazine anesthesia. A Kopf stereotaxic instrument was used to guide the injection cannula to the substantia nigra pars compacta. A sham surgery group received the same surgical procedure but saline instead of toxin. About 2 weeks after surgery and at two week intervals rats received three separate injections of d-amphetamine (3.0 mg/kg, ip, 15 min prior to recording sessions). Data shown here were from one control rat and one lesioned rat for the third drug treatment. Data were analyzed with the OFFLINEP.PAS program (FIGS. 18A–18C).

Results

Figure 7:
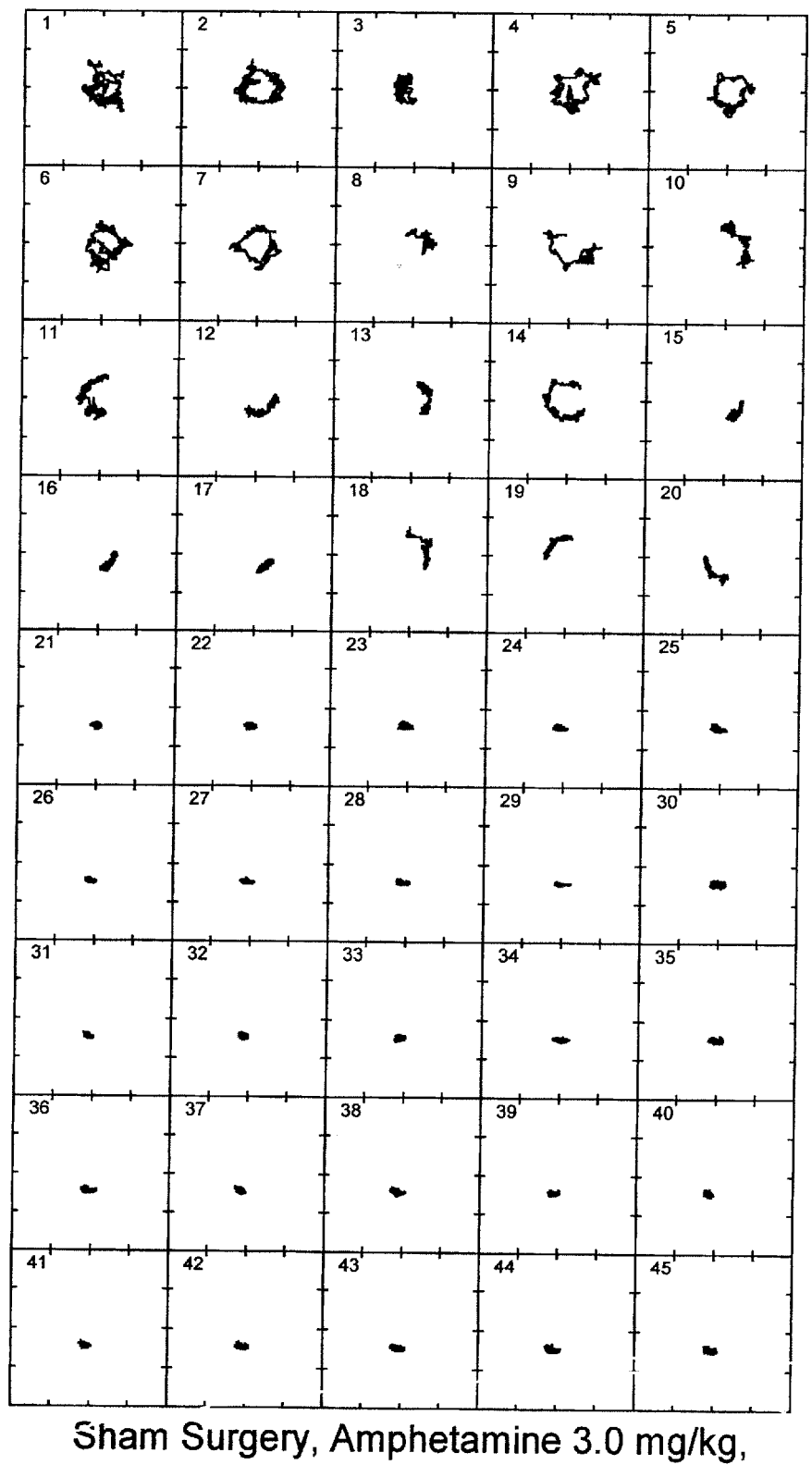
FIG. 7 is a series of 45 tracings of the movement of a control rat during the test period described in Example 3.
Figure 8:
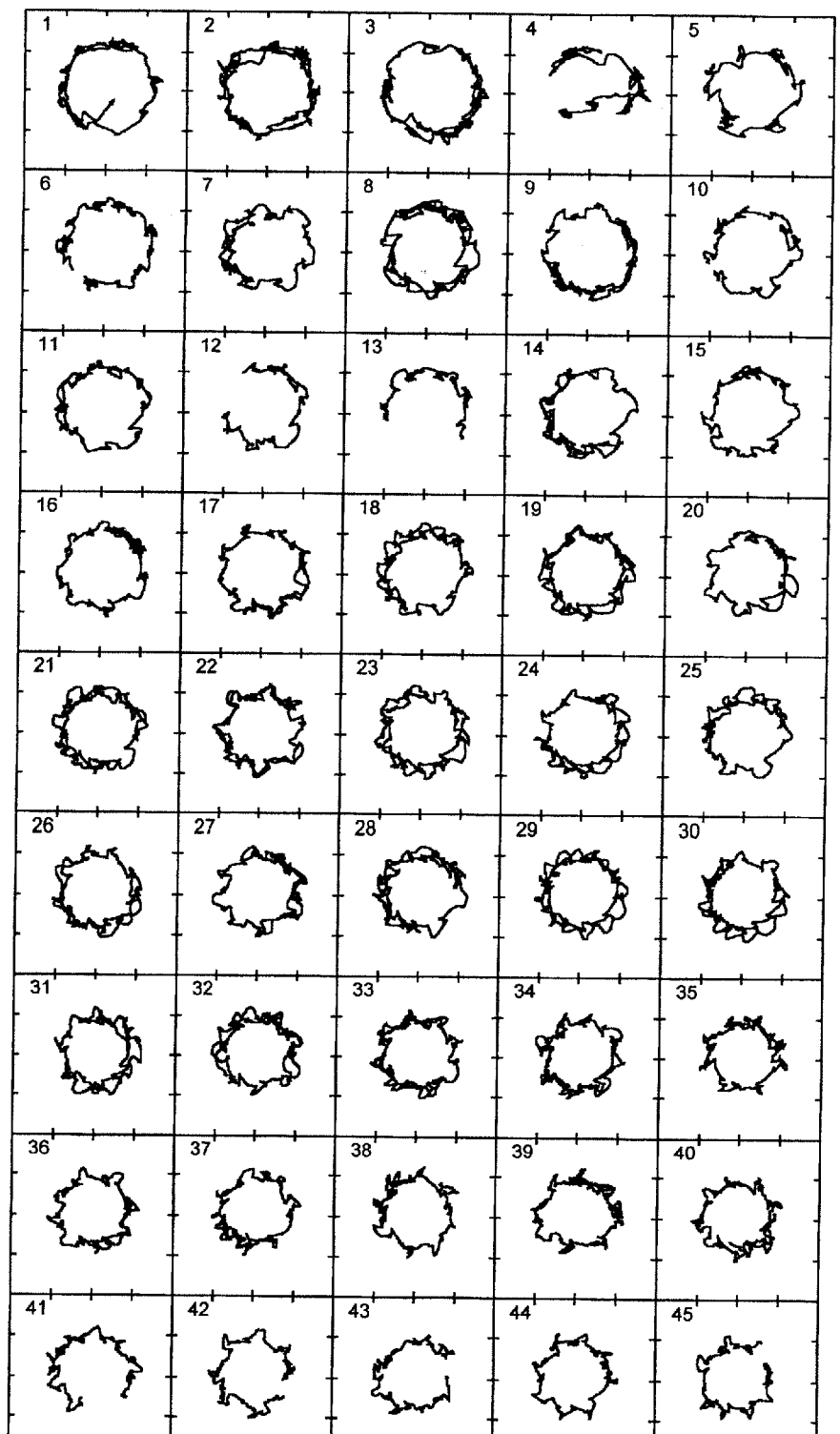
FIG. 8 is a series of 45 tracings of the movement of a 6-OHDA lesioned, amphetamine-treated rat during the test period described in Example 3.
Figure 9:
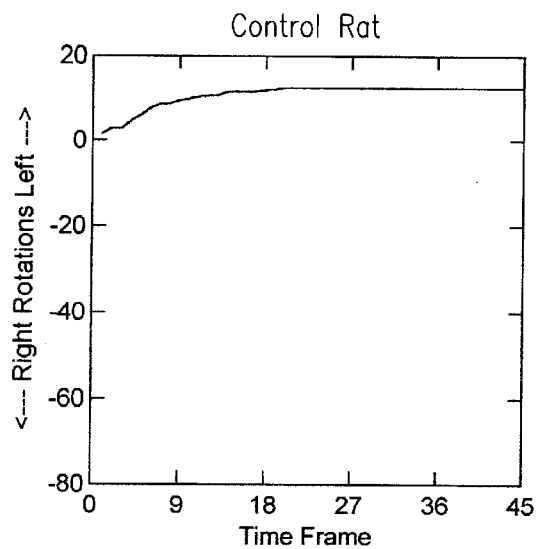
FIG. 9 is a graph of rotations versus time frame for the control rat of Example 3.
Figure 10:
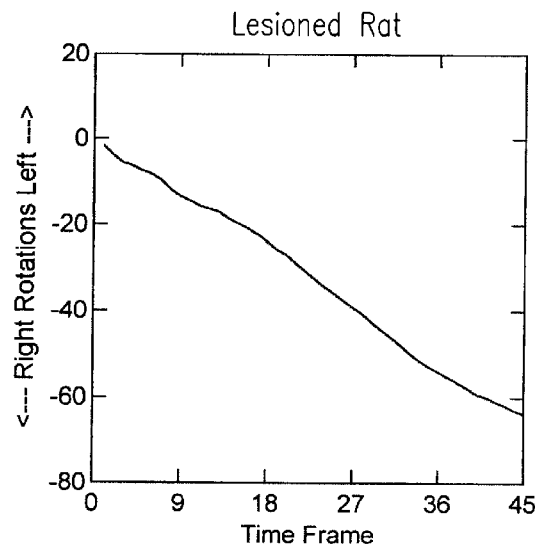
FIG. 10 is a graph of rotations versus time frame for the 6-OHDA lesioned, amphetamine-treated rat of Example 3.
Figure 11:
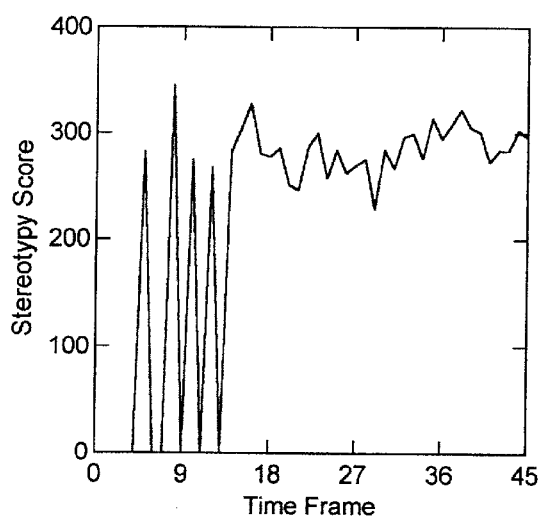
FIG. 11 is a graph of stereotypy score versus time frame for the control rat of Example 3.
Figure 12:
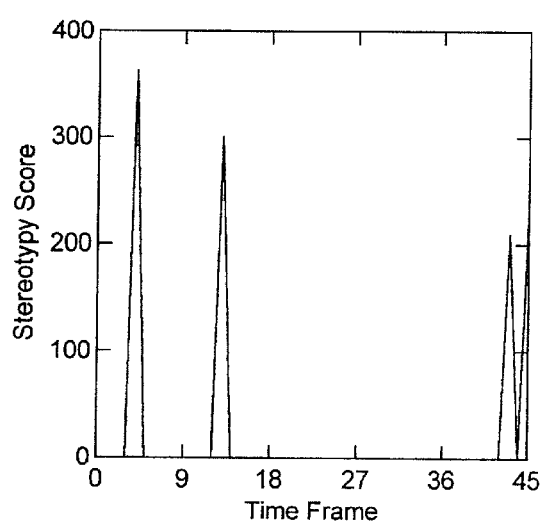
FIG. 12 is a graph of stereotypy score versus time frame for the 6-OHDA lesioned, amphetamine-treated rat of Example 3.

FIG. 7 shows the 45 frames of the 30 min session for the unlesioned rat under the influence of amphetamine, whereas FIG. 8 is a similar plot for the lesioned rat. Each square frame represents the perimeter of the square force plate chamber. The movement trajectory is round (particularly in FIG. 8) because the cylindrical insert presented a circular perimeter to the animal. This control rat showed very little locomotion, but the other analyses (FIGS. 9–12) indicated that the rat was primarily engaging in stereotypies. FIG. 8 depicts the robust rotational behavior of the lesioned rat treated with amphetamine. FIGS. 9 and 10 give the rotational data as a function of time within the session while FIGS. 11 and 12 give the stereotypy score for the same session. The control rat actually made 12 leftward rotations at the beginning of the session before giving way to continuous stereotypies. The lesioned rat made its 62 rotations to the right at an approximately linear rate and displayed only four bouts of high activity with low mobility (stereotypy score). The spiking nature of the plots in FIGS. 11 and 12 was caused by the fact that the stereotypy score for a 40.96-s time frame was zero if the space (30 mm) and time (10.24 s) low mobility criteria were not met at least once within a single frame. The stereotypy score plots give quantitative meaning to the phrase "continuous stereotypy", which, heretofore, could only be offered on a qualitative basis when time sampling observational methods were used. The stereotypies shown in FIG. 11 are continuous in the sense that from frame 14 to the end of the session the stereotypy score remains in the 250–300 range and does not once return to zero.

Conclusion

Rotational behavior in unilaterally lesioned rats was measured with unprecedented spatial and temporal precision and without the use of a harness-tether system. Any tendency of the rat to engage in stereotypies was simultaneously monitored.

Example 4

Mouse Strain Differences in Response to Daily Treatment with D-amphetamine

Purpose

Within the last decade mice have become the mammal of choice for studies of the effects of experimentally altered genetic endowment on brain and behavior. Hundreds of knockout mice (mice with targeted gene deletion, such as deletion of the gene for the dopamine D2 receptor) now exist. Scientists believe that these genetically altered mice may provide powerful insight into the working of the brain as it uses the environment to produce behavior. In the context of drug abuse and drug addiction, genetic influences are thought to affect vulnerability to drug dependence. One way to model these concepts in the laboratory is to use mice. These animals afford the means to investigate the interactions between genes, behavior-controlling procedures, and drugs.

In this Example, an investigation was undertaken to determine the differences in drug response and behavioral response in inbred strains of mice. An outbred strain was used as a type of control, because the outbred strain had genes and traits which the inbreds did not have. The inbred BALB/c and the C57BL/6 strains were chosen for this study, primarily because the C57BL/6 inbred strain reliably prefers ethanol, while other strains do not. This inbred strain also has peculiarities in its brain dopamine systems that make it a candidate for addiction studies.

One of the prominent contemporary theories of drug dependence involves the concept of sensitization. Sensitization is defined as an increasing response to the administration of a fixed dose of a drug as the drug is given multiples times, with the doses spaced far enough apart so that the first dose has been completely eliminated before the second dose is given. Robinson and Berridge have developed the theory that stimulant drugs become addictive partly because they sensitize the brain to their reinforcing effects. And this sensitization with repeated use leads to strong drug craving and drug seeking. In view of this theory, considerable interest has developed in sensitization phenomena attendant upon treatment with stimulants such as amphetamine or cocaine. Accordingly, using the force plate actometer and inbred strains of mice, we have now completed a study aimed at demonstrating genetic influences on behavioral sensitization to amphetamine.

Method

Male mice from Charles River Laboratories. BALB/c (n=32), C57BL/6 (n=32), and CD-1 (an outbred strain, n=32), were about 10 weeks old when the treatments began.

Four currently operating force plate chambers were used (the cylindrical insert was not present).

For each type of mouse, 4 dose groups were formed so that 8 mice of each strain received either saline, 1.0, 2.5 or 5.0 mg/kg d-amphetamine. On five consecutive days the mice received ip injections 1–2 min before being placed in the recording chambers for 30 min. Immediately before the drug session each mouse received a 30-min recording session preceded by a saline injection.

Data were analyzed with a version of OFFLINEP.PAS that divided the session into 9 intervals of 3 min and 24.8 s, instead of 45 frames as in the studies described in the preceding Examples. However, some graphic analyses were carried out with 45 frames. Analysis of variance was used to assess the effects of strain, dose, time within a session, and days of treatment (i.e., a 3×4×9×5 factorial design).

Results

Figure 13:
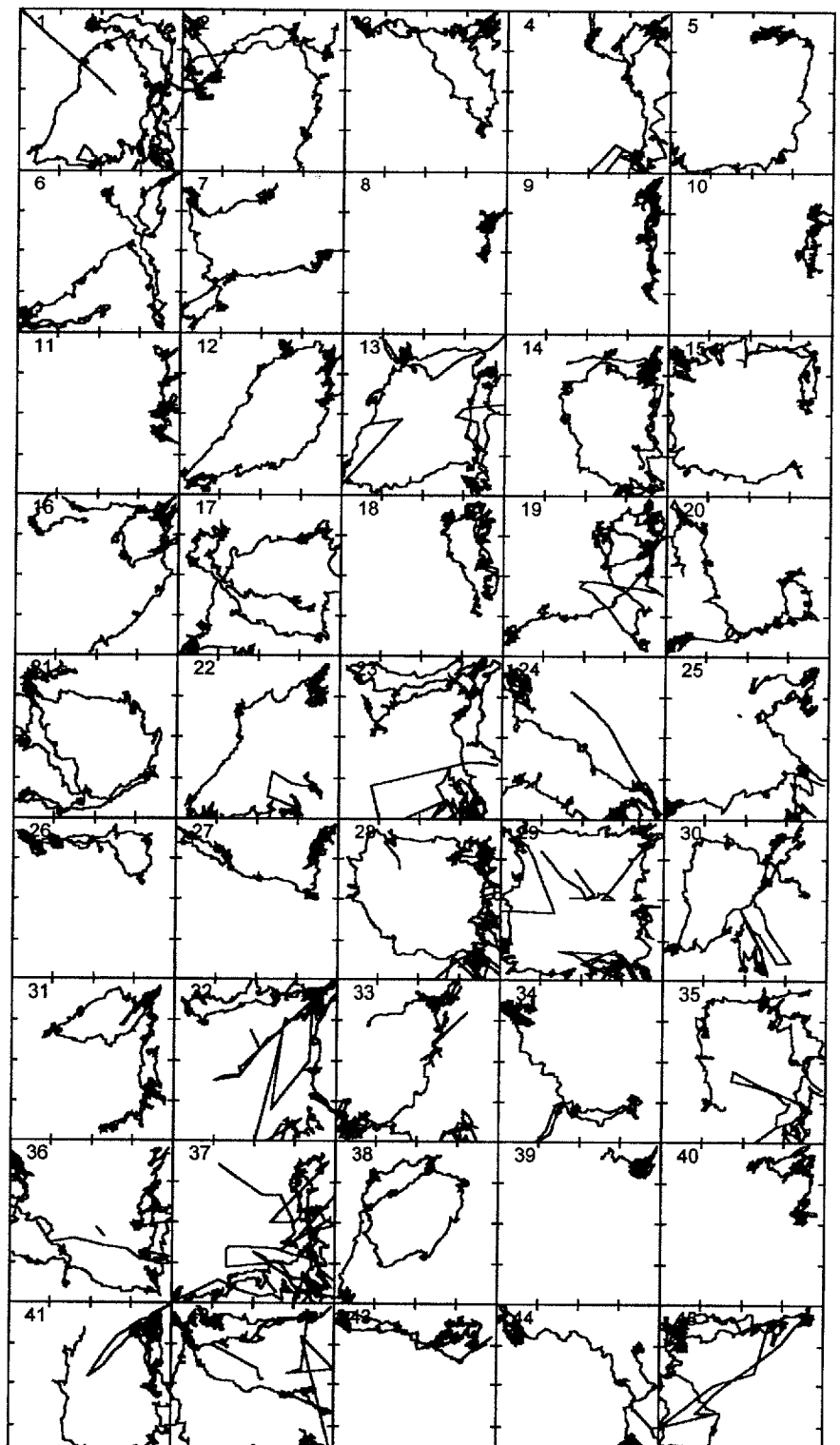
FIG. 13 is a series of 45 tracings of the movement of a control mouse obtained during the test period described in Example 4.
Figure 14:
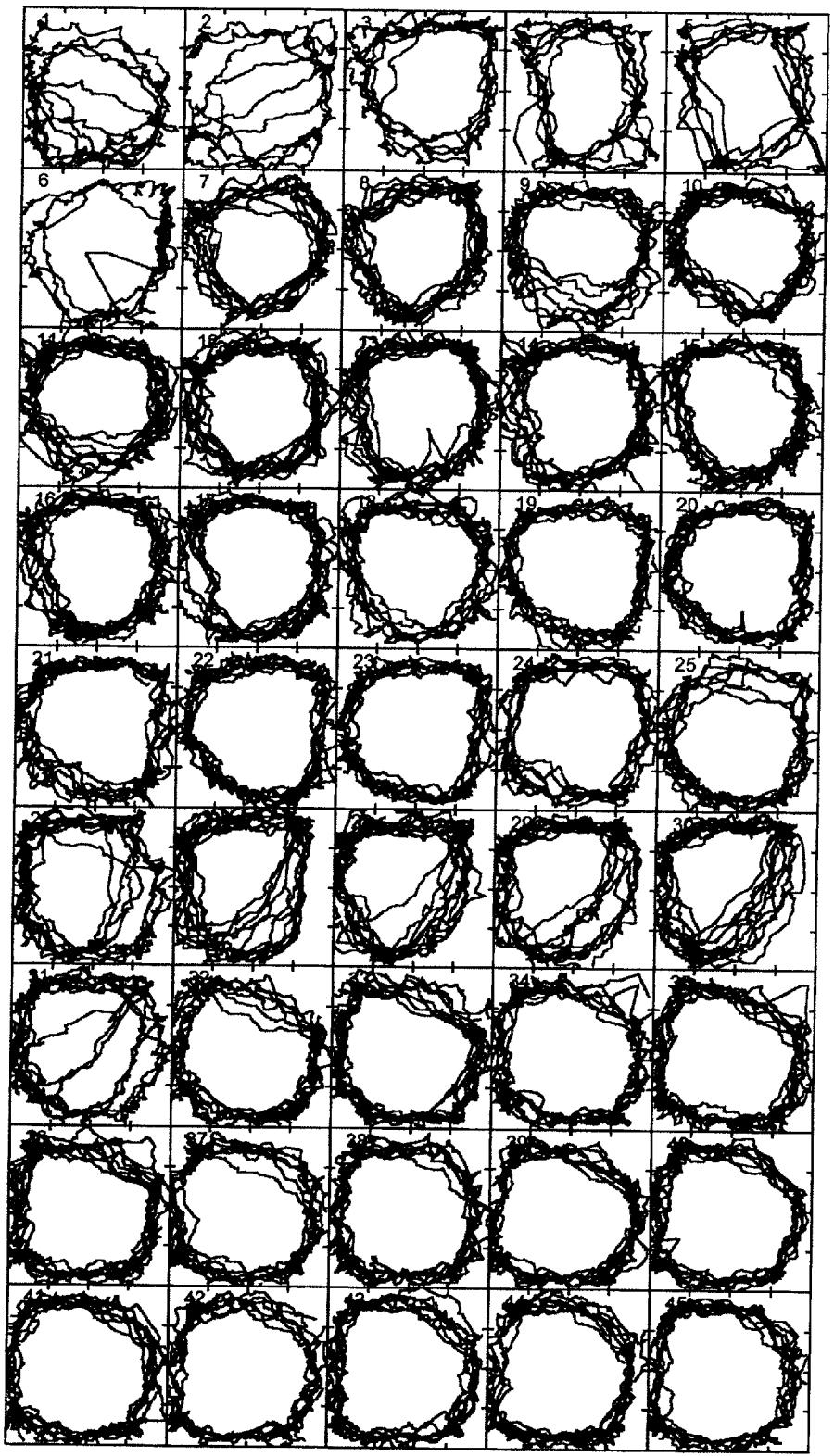
FIG. 14 is a series of 45 tracings of the movement of an amphetamine-treated mouse obtained during the test period described in Example 4.

FIG. 13 shows the frame-by-frame tracings of the movement trajectories of the center of force for one C57BL/6 mouse in the saline session. The straight lines are the result of the mouse jumping. This strain has a tendency to exhibit this behavior even when undrugged. This mouse's response to the fifth injection of 5.0 mg/kg of amphetamine is shown in FIG. 14. The locomotor stimulating effect of the drug is apparent.

Figure 15:
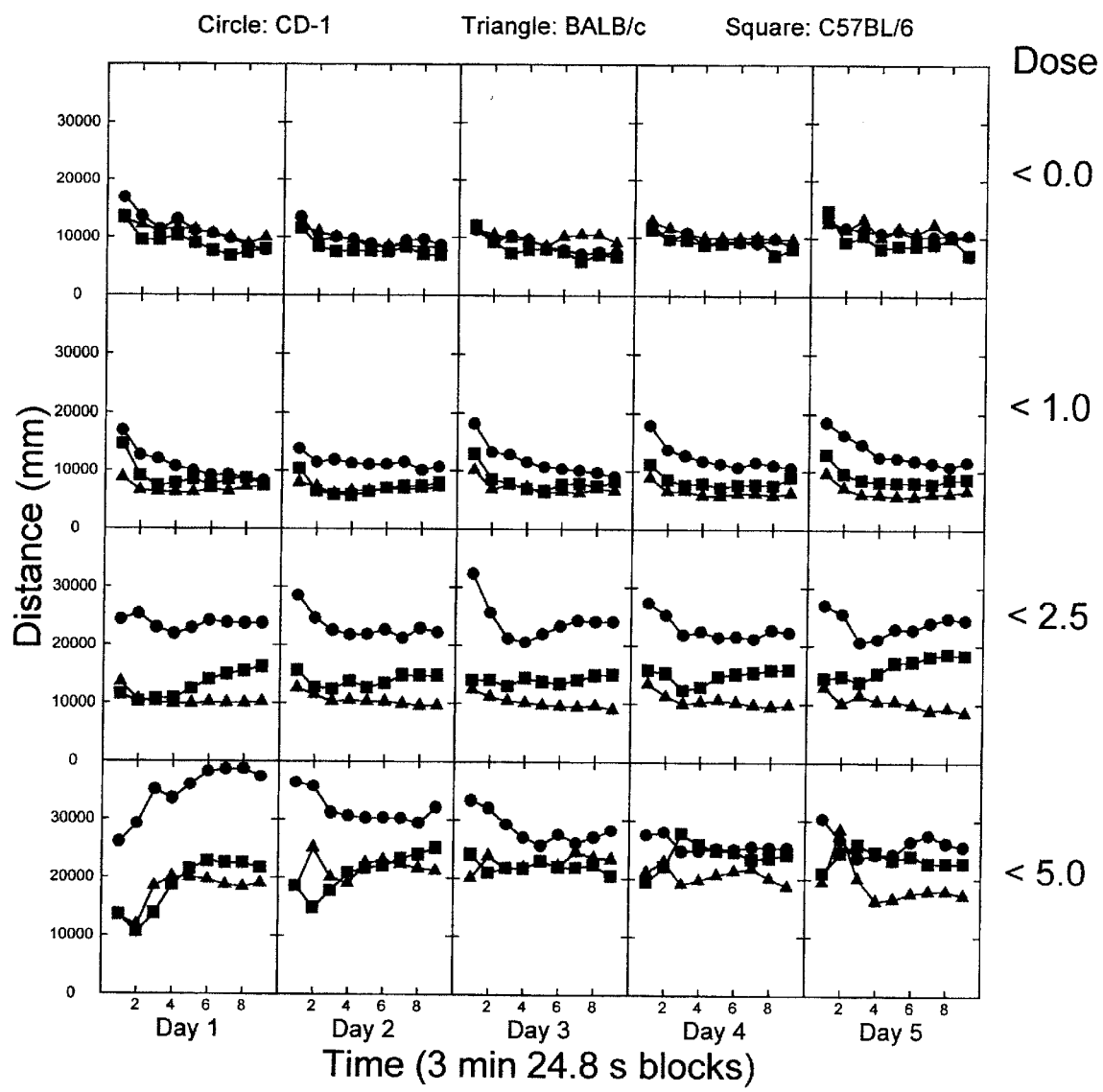
FIG. 15 is a parametric representation of the distance-traveled data obtained for the test mice of Example 4.

The distance-traveled data are presented parametrically in FIG. 15. In this Figure, mouse strain is coded by the type of plot symbol, dose effects read from top to bottom, and effects of repeated administrations of amphetamine read from left to right across. Analysis of variance confirmed significant effects of strain, $F(2,84)=65.296$, $p<0.001$, of dose, $F(3,84)=73.787$, $p<0.001$, and of strain-by-dose interaction, $F(6,84)=9.293$, $p<0.001$. Strain differences were apparent after amphetamine treatment, but not apparent in the saline treatment conditions. The 2.5 mg/kg dose produced the clearest consistent separation among the three strains; CD-1's were stimulated the most and the BALB/c's the least. Also at the 2.5 mg/kg dose the C57BL/6 mouse showed a sensitization effect across the 5 treatment days. Results for the distance variable are truncated here for the sake of brevity.

Figure 16:
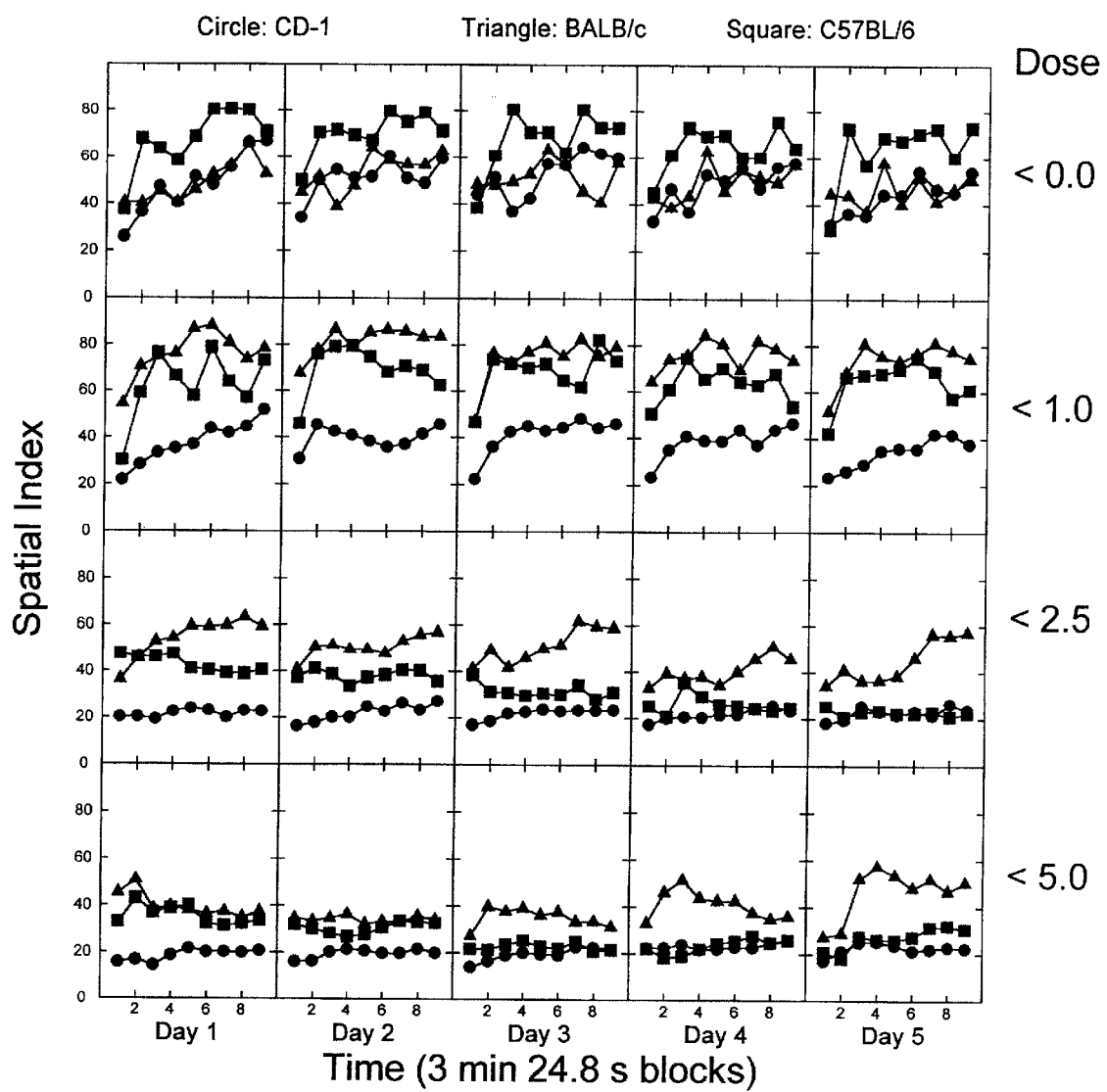
FIG. 16 is a parametric representation of the spatial index versus time obtained for the test mice of Example 4.

FIG. 16 gives the results for the graphic analysis using the spatial statistic. This index varies in relation to the degree to which a mouse distributes its behavior across 64-equal sized square sectors (35 mm on a side) of the 280×280 mm force plate. The larger the index the more concentrated in space is the animal's movements. Here too analysis of variance supported significant effects of strain, $F(2,84)=26.132$, $p<0.001$, of dose, $F(3,84)=38.192$, $p<0.001$, and of strain-by-dose interaction, $F(6,84)=4.991$, $p<0.001$. At the two highest doses, the BALB/c mouse displayed a greater tendency to restrict its movements in space, and this tendency sensitizes. (grows) across treatment days at the highest dose. Interestingly, the spatial index suggests differences among the strains even in the absence of amphetamine treatment (see FIG. 16). Strain differences were not apparent in the saline condition for the Distance variable (see FIG. 15).

Conclusion

The analytical methods afforded by the force plate actometer provides a means for distinguishing between the three strains of mice under both drug and non-drug conditions. Moreover, sensitization effects of amphetamine probably are strain dependent and therefore depend in part on the genetic endowment of the mouse. These data demonstrate that the force plate actometer detects the locomotor stimulation effect of amphetamine reported in studies using photobeam actometers.

Example 5

Genetic Influences on Response to Ethanol

Purpose

Genetically defined mice are increasingly being used in an effort to discover brain mechanisms that affect sensitivity to the effect of ethanol. Altered sensitivities are thought to underlie, in part, the development of alcoholism in human populations. The force plate actometer has been used to investigate differences in sensitivity to ethanol in inbred strains of mice. Of particular interest was the sensitivity of the C57BL/6 strain, a strain known to prefer 10% ethanol over water in a two bottle preference test.

Method

The subjects were 12 male mice of each of the three strains: CD-1, BALB/c, and C57BL/6 obtained from Charles River Laboratories.

The force plate actometer was used as described above.

The mice were subdivided into groups of 6 each. One group received saline, and the corresponding other group of that strain received a dose of 2.0 g/kg of ethanol in a 20% aqueous solution. This was the first exposure to the chamber for these mice. Within 1–2 min of the ip injection the mice were placed in the chamber and behavior was recorded for 30 min.

The distance data were divided into 6 blocks of 5 min each, and analysis of variance (3 strains×saline vs drug×6 time blocks) was used to establish the presence of effects.

Results

Figure 17:
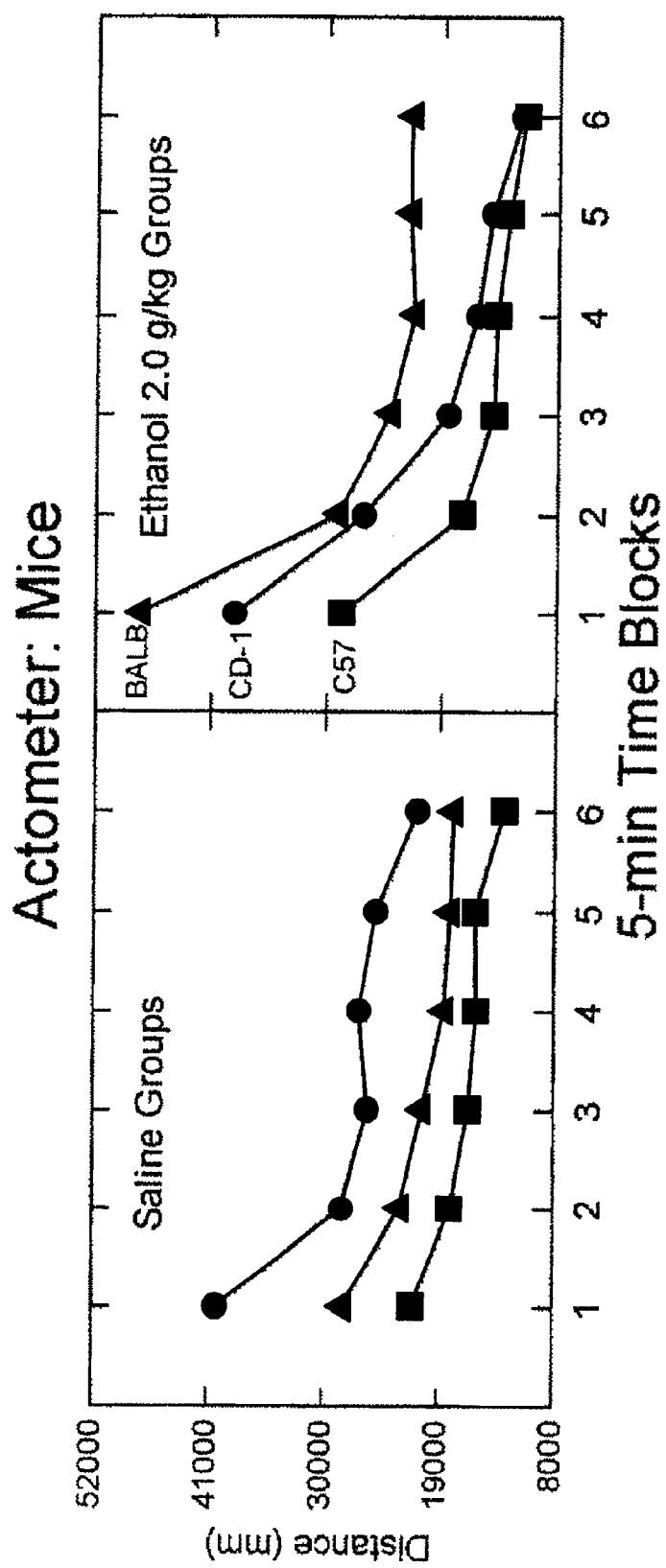
FIG. 17 illustrates comparative graphs of distance versus time blocks for control and ethanol-treated mice obtained during the test of Example 5.

The data shown in FIG. 17 indicate that, compared to saline treated mice with equal experience in the actometer, the ethanol mice were initially stimulated, but to differing degrees (BALB/c displayed the greatest proportional increase in activity). In addition, the strains appeared to differ in the levels of activity reached by the end of the ethanol session. Analysis of variance revealed the following effects: a significant effect of strain, $F(2,30)=5.788$, $p=0.007$; a significant strain-by-ethanol interaction, $F(2,30)=3.257$, $p=0.05$; a significant time-blocks effect, $F(5,150)=65.225$, $p<0.001$; a significant time-by-strain interaction, $F(10,150)=2.021$, $p=0.035$; and a significant-time-by-ethanol interaction, $F(5,150)=7.629$, $p<0.001$. The significant strain-by-ethanol interaction indicates a differential strain response to ethanol. For example, during the first time block the BALB/c strain showed the greater amount of ethanol related locomotor stimulation, and the CD-1 strain exhibited the least stimulation compared to the saline control mice of these strains.

Conclusions

The implication of this study is that both strain and ethanol effects are robust with these methods. In addition, these results show that the force plate actometer is useful in the laboratory study of the factors (genetic, behavioral, pharmacological) that influence sensitivity to ethanol.

We claim:

1. A device for testing an in vivo subject, comprising:
   a first plate presenting an upper surface adapted to support said subject during testing;
   at least three transducers operably coupled with said first plate, each of said transducers operable to sense a parameter resulting from movement of said subject on said plate upper surface, and to generate an output correlated with said sensed parameter;
   a second plate spaced from said first plate and operably coupled with said transducers fixing the locations of said transducers relative to each other; and
   a processor coupled with said transducers to receive said outputs, said processor operable to perform calculations and recordings using said outputs to determine at least one attribute of said movement of said subject.

2. The device of claim 1, said processor operable to determine the variation over time of the force exerted by said subject on said plate.

3. The device of claim 1, said processor operable to determine an attribute selected from the group consisting of the position of said subject on said plate, the distance traveled by the subject over a defined time period, the angle and direction of rotation of movement of the subject, a spatial statistic of the movement of the subject, stereotypy, tremor, and rearing of the subject.

4. The device of claim 1, said transducers selected from the group consisting of force and pressure transducers.

5. The device of claim 4, said transducers being force transducers.

6. The device of claim 1, there being four of said transducers.

7. The device of claim 1, said processor being a computer.

8. The device of claim 1, including a subject-confining enclosure fixedly located above and out of contact with said plate.

9. The device of claim 8, said enclosure being substantially square in plan configuration.

10. The device of claim 8, said enclosure being substantially circular in plan configuration.

11. The device of claim 8, said enclosure including an openable door permitting access to the interior of the enclosure.

12. The device of claim 1, said processor operable to repeatedly perform said calculations during a test period.

13. The device of claim 12, the interval between successive calculations being up to about 1 second.

14. The device of claim 13, said interval being from about 0.01–0.1 seconds.

15. A method of testing an in vivo subject comprising the steps of:
placing said subject on a plate presenting an upper surface, and allowing the subject to ambulate on said plate;
sensing from at least three fixed locations on said plate parameters related to the force exerted by said subject on the plate, and generating outputs correlated with the sensed parameters; and
using said outputs, calculating at least one attribute of said ambulation of said subject.

16. The method of claim 15, including the step of calculating the variation over time of the force exerted by said subject on said plate.

17. The method of claim 15, including the step of calculating an attribute selected from the group consisting of the position of said subject on said plate, the distance traveled by the subject over a defined time period, the angle and direction of rotation of ambulation of the subject, a spatial statistic of the ambulation of the subject, stereotypy, tremor, and rearing of the subject.

18. The method of claim 15, including the step of using transducers coupled to said plate to sense said parameters and to generate said outputs, said transducers selected from the group consisting of force and pressure transducers.

19. The method of claim 18, said transducers being force transducers.

20. The method of claim 15, there being four of said transducers supporting said plate.

21. The method of claim 15, including the step of using a computer to carry out said calculation.

22. The method of claim 15, including the step of confining said subject to a predetermined area on said plate.

23. The method of claim 15, including the step of repeatedly performing said calculation and recording results during a test period.

24. The method of claim 23, the interval between successive calculations being up to about 1 second.

25. The method of claim 24, said interval being from about 0.01–0.1 seconds.

* * * * *